(12) United States Patent
Caputo et al.

(10) Patent No.: US 7,090,808 B2
(45) Date of Patent: Aug. 15, 2006

(54) APPARATUS FOR TESTING STERILIZATION METHODS AND MATERIALS

(75) Inventors: Ross A. Caputo, Long Grove, IL (US); Robert R. Reich, Jr., Grayslake, IL (US); Robert J. Thrash, St. Charles, IL (US); Jimmy Fisher, Hawthorn Woods, IL (US); Davoud Khorzad, Lake Forest, IL (US); Thomas F. Cullen, Des Plaines, IL (US)

(73) Assignee: Pharmaceutical Systems, Inc., Mundelein, IL (US)

( * ) Notice: Subject to any disclaimer, the term of this patent is extended or adjusted under 35 U.S.C. 154(b) by 842 days.

(21) Appl. No.: 09/901,389

(22) Filed: Jul. 9, 2001

(65) Prior Publication Data

US 2003/0012689 A1    Jan. 16, 2003

(51) Int. Cl.
*A61L 9/00* (2006.01)
*B01J 19/08* (2006.01)
*G01N 21/00* (2006.01)

(52) U.S. Cl. .............................. 422/305; 422/1; 422/3; 422/4; 422/28; 422/32; 422/119; 422/186.04; 356/437; 356/442

(58) Field of Classification Search .................... 422/1, 422/3–4, 28, 32–34, 55, 61–62, 119, 186.04, 422/300, 305; 356/437, 442
See application file for complete search history.

(56) References Cited

U.S. PATENT DOCUMENTS 2,491,732 A    12/1949   Hawkinson et al. ........... 203/6

(Continued)

FOREIGN PATENT DOCUMENTS

EP    0 291 616    11/1988

(Continued)

OTHER PUBLICATIONS

Association for the Advancement of Medical Instrumentation, "*Standard for BIER/Steam Vessels.*" (1981).
Association for the Advancement of Medical Instrumentation, "*BIER/Steam Vessels*," (1992).

(Continued)

*Primary Examiner*—Richard Crispino
*Assistant Examiner*—Monzer R. Chorbaji
(74) *Attorney, Agent, or Firm*—Bryan Cave LLP; Stephen P. Gilbert; Charles M. Avigliano

(57) ABSTRACT

Apparatus and method for testing one or more sterilization indicators (e.g., biological indicators or chemical indicators) or other articles by contacting them under controlled sterilization conditions with a flowing antimicrobial gas containing hydrogen peroxide vapor are disclosed. This invention also provides apparatus and method for testing sterilization processes that use a flowing antimicrobial gas containing hydrogen peroxide vapor under controlled sterilization conditions, or for testing materials for such processes under controlled sterilization conditions, or for testing both such processes and such materials under controlled sterilization conditions. There can be an essentially square-wave contact of the sterilization indicators or other articles with the antimicrobial gas (i.e., short rise time to reach full concentration of the antimicrobial gas in contact with the sterilization indicators or other articles and short fall time to remove all of the antimicrobial gas from contact with the sterilization indicators or other articles). A preferred way of generating a substantially constant flow of antimicrobial gas of substantially constant hydrogen peroxide concentration may be used to generate the antimicrobial gas. A preferred way of determining the hydrogen peroxide concentration in the antimicrobial gas may be used.

53 Claims, 14 Drawing Sheets

U.S. PATENT DOCUMENTS

| | | | |
|---|---|---|---|
| 3,851,436 A | 12/1974 | Fraser et al. | 53/434 |
| 3,948,601 A | 4/1976 | Fraser et al. | 422/23 |
| 3,992,154 A * | 11/1976 | Whitbourne et al. | 422/34 |
| 4,169,123 A | 9/1979 | Moore et al. | 422/29 |
| 4,169,124 A | 9/1979 | Forstrom et al. | 422/33 |
| 4,230,663 A | 10/1980 | Forstrom et al. | 422/33 |
| 4,289,728 A | 9/1981 | Peel et al. | 422/24 |
| 4,296,068 A | 10/1981 | Hoshino | 422/62 |
| 4,314,344 A | 2/1982 | Johns et al. | 364/500 |
| 4,321,232 A | 3/1982 | Bithell | 422/23 |
| 4,366,125 A | 12/1982 | Kodera et al. | 422/295 |
| 4,401,755 A | 8/1983 | Weaver | 435/34 |
| 4,427,772 A | 1/1984 | Kodera et al. | 435/27 |
| 4,437,567 A | 3/1984 | Jeng | 206/210 |
| 4,514,361 A | 4/1985 | Hirsch | 422/26 |
| 4,525,265 A | 6/1985 | Abe et al. | 204/403 |
| 4,528,268 A | 7/1985 | Andersen et al. | 455/31 |
| 4,642,165 A | 2/1987 | Bier | 203/12 |
| 4,643,876 A | 2/1987 | Jacobs et al. | 422/23 |
| 4,671,936 A | 6/1987 | Barron | 422/55 |
| 4,680,163 A | 7/1987 | Blidschun et al. | 422/28 |
| 4,707,334 A | 11/1987 | Gerhard | 422/28 |
| 4,717,661 A | 1/1988 | McCormick et al. | 435/31 |
| 4,742,667 A | 5/1988 | Muller et al. | 53/167 |
| 4,743,537 A | 5/1988 | McCormick et al. | 435/296 |
| 4,756,882 A | 7/1988 | Jacobs et al. | 422/23 |
| 4,795,707 A | 1/1989 | Niiyama et al. | 435/288 |
| 4,797,255 A | 1/1989 | Hatanaka et al. | 422/28 |
| 4,828,797 A | 5/1989 | Zwarun et al. | 422/55 |
| 4,839,291 A | 6/1989 | Welsh et al. | 435/296 |
| 4,843,867 A | 7/1989 | Cummings | 73/23 |
| 4,850,716 A | 7/1989 | Baker et al. | 374/160 |
| RE33,007 E | 8/1989 | Bier | 203/12 |
| 4,863,688 A * | 9/1989 | Schmidt et al. | 422/28 |
| 4,883,641 A | 11/1989 | Wicks et al. | 422/50 |
| 4,885,253 A | 12/1989 | Kralovic | 435/296 |
| 4,909,999 A | 3/1990 | Cummings et al. | 422/298 |
| 4,914,034 A | 4/1990 | Welsh et al. | 435/296 |
| 4,956,145 A | 9/1990 | Cummings et al. | 422/28 |
| 4,992,247 A | 2/1991 | Foti | 422/304 |
| 5,007,232 A | 4/1991 | Caudill | 53/426 |
| 5,078,976 A | 1/1992 | Shibauchi et al. | 422/28 |
| 5,084,239 A | 1/1992 | Moulton et al. | 422/22 |
| 5,097,130 A | 3/1992 | Koashi et al. | 250/339 |
| 5,114,670 A | 5/1992 | Duffey | 422/24 |
| 5,115,166 A | 5/1992 | Campbell et al. | 315/111.21 |
| 5,139,957 A | 8/1992 | Grack | 436/135 |
| 5,152,968 A | 10/1992 | Foti et al. | 422/304 |
| 5,167,927 A | 12/1992 | Karlson | 422/90 |
| 5,178,829 A | 1/1993 | Moulton et al. | 422/23 |
| 5,178,841 A | 1/1993 | Vokins et al. | 422/298 |
| 5,180,553 A | 1/1993 | Singer et al. | 422/28 |
| 5,184,046 A | 2/1993 | Campbell | 315/111.21 |
| 5,186,893 A | 2/1993 | Moulton et al. | 422/23 |
| 5,200,146 A | 4/1993 | Goodman | 422/23 |
| 5,244,629 A | 9/1993 | Caputo et al. | 422/22 |
| 5,258,162 A | 11/1993 | Andersson et al. | 422/28 |
| 5,288,460 A | 2/1994 | Caputo et al. | 422/23 |
| 5,317,896 A | 6/1994 | Sheth et al. | 73/29.01 |
| 5,325,020 A | 6/1994 | Campbell et al. | 315/111.21 |
| 5,364,590 A | 11/1994 | Hillebrenner | 422/28 |
| 5,376,332 A | 12/1994 | Martens et al. | 422/23 |
| 5,413,758 A | 5/1995 | Caputo et al. | 422/22 |
| 5,413,759 A | 5/1995 | Campbell et al. | 422/23 |
| 5,413,760 A | 5/1995 | Campbell et al. | 422/24 |
| 5,439,643 A | 8/1995 | Liebert | 422/25 |
| 5,445,792 A | 8/1995 | Rickloff et al. | 427/28 |
| 5,470,548 A | 11/1995 | Hillebrenner | 422/295 |
| 5,472,664 A | 12/1995 | Campbell et al. | 422/23 |
| 5,474,908 A | 12/1995 | Kurono et al. | 435/28 |
| 5,482,684 A * | 1/1996 | Martens et al. | 422/119 |
| 5,486,459 A | 1/1996 | Burnham et al. | 435/31 |
| 5,492,672 A | 2/1996 | Childers et al. | 422/28 |
| 5,498,526 A | 3/1996 | Caputo et al. | 435/31 |
| 5,503,807 A | 4/1996 | Griffiths et al. | 422/186.04 |
| 5,508,009 A | 4/1996 | Rickloff et al. | 422/292 |
| 5,512,244 A | 4/1996 | Griffiths et al. | 422/23 |
| 5,516,489 A | 5/1996 | Melgaard et al. | 422/82.13 |
| 5,516,648 A | 5/1996 | Malchesky et al. | 435/31 |
| 5,518,591 A | 5/1996 | Pulliainen et al. | 205/782 |
| 5,525,295 A | 6/1996 | Pflug et al. | 422/27 |
| 5,527,508 A | 6/1996 | Childers et al. | 422/33 |
| 5,534,221 A | 7/1996 | Hillebrenner et al. | 422/33 |
| 5,556,607 A | 9/1996 | Childers et al. | 422/300 |
| 5,593,649 A | 1/1997 | Fisher et al. | 422/305 |
| 5,600,142 A | 2/1997 | Van Den Berg et al. | 250/339.13 |
| 5,603,895 A | 2/1997 | Martens et al. | 422/23 |
| 5,608,156 A | 3/1997 | Ando et al. | 73/31.06 |
| 5,620,656 A | 4/1997 | Wensky et al. | 422/28 |
| 5,633,424 A | 5/1997 | Graves et al. | 588/227 |
| 5,645,796 A | 7/1997 | Caputo et al. | 422/22 |
| 5,650,693 A | 7/1997 | Campbell et al. | 315/111.21 |
| 5,667,753 A | 9/1997 | Jacobs et al. | 422/29 |
| 5,674,450 A | 10/1997 | Lin et al. | 422/29 |
| 5,739,004 A | 4/1998 | Woodson | 435/31 |
| 5,750,184 A | 5/1998 | Imburgia | 427/2.13 |
| 5,753,196 A | 5/1998 | Martens et al. | 422/293 |
| 5,770,393 A | 6/1998 | Dalmasso et al. | 435/31 |
| 5,770,739 A | 6/1998 | Lin et al. | 548/335.5 |
| 5,779,973 A | 7/1998 | Edwards et al. | 422/28 |
| 5,783,146 A | 7/1998 | Williams, Jr. | 422/26 |
| 5,788,925 A | 8/1998 | Pai et al. | 422/3 |
| 5,789,175 A | 8/1998 | Priest | 436/1 |
| 5,792,435 A | 8/1998 | Mueller et al. | 422/292 |
| 5,824,553 A | 10/1998 | McCormick et al. | 436/1 |
| 5,830,409 A | 11/1998 | Childers et al. | 422/30 |
| 5,830,683 A | 11/1998 | Hendricks et al. | 435/31 |
| 5,843,374 A | 12/1998 | Sizer et al. | 422/24 |
| 5,847,392 A | 12/1998 | Van Den Berg et al. | 250/339.09 |
| 5,847,393 A | 12/1998 | Van Den Berg et al. | 250/339.13 |
| 5,866,356 A | 2/1999 | Albert et al. | 435/31 |
| 5,870,885 A | 2/1999 | Biddle et al. | 53/436 |
| 5,872,004 A | 2/1999 | Bolsen | 435/287.4 |
| 5,872,359 A | 2/1999 | Stewart et al. | 250/339.12 |
| 5,876,666 A | 3/1999 | Lin et al. | 422/29 |
| 5,892,229 A | 4/1999 | Crozier et al. | 250/339.13 |
| 5,904,897 A | 5/1999 | Kendall et al. | 422/28 |
| 5,911,950 A | 6/1999 | Chen et al. | 422/28 |
| 5,916,816 A | 6/1999 | Read | 436/166 |
| 5,923,432 A | 7/1999 | Kral | 356/432 |
| 5,928,948 A | 7/1999 | Malchesky | 436/2 |
| 5,938,917 A | 8/1999 | Mulchandani | 205/782 |
| 5,939,033 A | 8/1999 | Kendall et al. | 422/305 |
| 5,942,408 A | 8/1999 | Christensen et al. | 455/31 |
| 5,942,754 A | 8/1999 | Yamaguchi et al. | 250/339.12 |
| 5,972,199 A | 10/1999 | Heller et al. | 205/777.5 |
| 5,980,825 A | 11/1999 | Addy et al. | 422/33 |
| 5,989,852 A | 11/1999 | Hendricks et al. | 435/31 |
| 6,030,579 A | 2/2000 | Addy et al. | 422/28 |
| 6,036,918 A | 3/2000 | Kowanko | 422/33 |
| 6,039,922 A | 3/2000 | Swank et al. | 422/24 |
| 6,056,918 A | 5/2000 | Palaniappan et al. | 422/24 |
| 6,071,483 A | 6/2000 | Pastore | 422/255 |
| 6,075,246 A | 6/2000 | Stock | 250/343 |
| 6,077,480 A | 6/2000 | Edwards et al. | 422/28 |
| 6,094,523 A | 7/2000 | Zelina et al. | 392/399 |
| 6,094,887 A | 8/2000 | Swank et al. | 53/426 |
| 6,096,265 A | 8/2000 | Mezger et al. | 422/28 |
| 6,120,730 A | 9/2000 | Palaniappan et al. | 422/28 |
| 6,132,680 A | 10/2000 | Addy et al. | 422/35 |
| 6,145,276 A | 11/2000 | Palm et al. | 53/426 |

| | | | |
|---|---|---|---|
| 6,149,878 A | 11/2000 | Jacob et al. | 422/186.04 |
| 6,156,267 A | 12/2000 | Pai et al. | 422/3 |
| 6,174,502 B1 | 1/2001 | Addy et al. | 422/242 |
| 6,183,691 B1 | 2/2001 | Swank et al. | 422/24 |
| 6,189,368 B1 | 2/2001 | Ichida et al. | 73/31.06 |
| 6,203,756 B1 | 3/2001 | Lin et al. | 422/33 |
| 6,406,666 B1 | 6/2002 | Cicha et al. | 422/28 |
| 6,432,357 B1 * | 8/2002 | Richard et al. | 422/34 |
| 6,594,017 B1 * | 7/2003 | Menden | 356/441 |
| 6,736,379 B1 | 5/2004 | Wegner et al. | 261/127 |
| 2002/0134051 A1 | 9/2002 | Kurth | 53/425 |

FOREIGN PATENT DOCUMENTS

| | | |
|---|---|---|
| EP | 0 321 908 | 6/1989 |
| EP | 1016421 | 7/2000 |
| GB | 1582060 | 12/1980 |
| GB | 2089213 | 6/1982 |
| JP | 2-276950 | 11/1990 |
| WO | WO 94/23813 | 10/1994 |
| WO | WO 00/33967 | 6/2000 |
| WO | WO 00/57927 | 10/2000 |
| WO | WO 00/65344 | 11/2000 |
| WO | WO 01/13964 | 3/2001 |
| WO | WO 01/44053 | 6/2001 |

OTHER PUBLICATIONS

Association for the Advancement of Medical Instrumentation, "Standard for BIER/EO Gas Vessels" (1982).
Association for the Advancement of Medical Instrumentation, "BIER/EO Gas Vessels," (1992).
Joslyn Valve Corp., "Biological Indicator Evaluator Resistometer (BIER)—Laboratory Test Systems For Steam And Ethylene Oxide," 4 pages (undated).
U.S. Phamacopoeia XXII, Official Monograph "Biological Indicators," pp. 1625-1626 (undated).
Herzberg, Molecular Spectra and Molecular Structure, II. Infrared and Raman Spectra of Polyatomic Molecules, p. 53 (1945).
Klapes et al., "Vapor-Phase Hydrogen Peroxide as a Surface Decontaminant and Sterilant," Applied and Environmental Microbiology, vol. 56, No. 2, pp. 503-506 (1990).
Skoog, Holler, Nieman, Principles of Instrumental Analysis. (5$^{th}$ Edition), pp. 311-312 (1998).
Steinfeld, Molecules and Radiation—An Introduction to Modern Molecular Spectroscopy, p. 229 (1974).
International Search Report for PCT Application Serial No. PCT/US02/21501, mailed Nov. 5, 2002.
International Search Report for PCT Application Serial No. PCT/US02/21500, mailed Nov. 5, 2002.
International Search Report for PCT Application No. PCT/US02/21499, mailed Dec. 18, 2002.
International "Written Opinion" for PCT Application Serial No. PCT/US02/21501, mailed Jun. 5, 2003.
International "Written Opinion" for PCT Application Serial No. PCT/US02/21501, mailed Jun. 5, 2003.
Supplementary European Search Report mailed on Oct. 28, 2004 for related European Application No. 02746911.3.
Supplementary European Search Report mailed on Sep. 12, 2005 for related European Application No. 02742394.6.

* cited by examiner

| Sample | Count 1 | Count 2 | log (Sample 1) | log (Sample 2) | log Average | Range | Log Reduction |
|---|---|---|---|---|---|---|---|
| 1 | 750 | 710 | 2.8751 | 2.8513 | 2.8632 | 0.0238 | 3.1368 |
| 3 | 1070 | 890 | 3.0294 | 2.9494 | 2.9894 | 0.0800 | 3.0106 |
| 4 | 780 | 970 | 2.8921 | 2.9868 | 2.9394 | 0.0947 | 3.0606 |
| 5 | 370 | 480 | 2.5682 | 2.6812 | 2.6247 | 0.1130 | 3.3753 |
| 6 | 1280 | 1560 | 3.1072 | 3.1931 | 3.1502 | 0.0859 | 2.8498 |
| 7 | 360 | 260 | 2.5563 | 2.4150 | 2.4856 | 0.1413 | 3.5144 |
| 8 | 680 | 650 | 2.8315 | 2.8129 | 2.8227 | 0.0196 | 3.1773 |
| 10 | 820 | 790 | 2.9138 | 2.8976 | 2.9057 | 0.0162 | 3.0943 |
| 12 | 610 | 600 | 2.7853 | 2.7782 | 2.7817 | 0.0072 | 3.2183 |
| 13 | 1200 | 1190 | 3.0792 | 3.0755 | 3.0774 | 0.0036 | 2.9226 |
| 14 | 670 | 600 | 2.8261 | 2.7782 | 2.8021 | 0.0479 | 3.1976 |
| 15 | 620 | 710 | 2.7924 | 2.8513 | 2.8218 | 0.0589 | 3.1782 |
| 16 | 230 | 150 | 2.3617 | 2.1761 | 2.2689 | 0.1856 | 3.7311 |
| 17 | 440 | 360 | 2.6435 | 2.5563 | 2.5999 | 0.0872 | 3.4001 |
| 19 | 2130 | 1840 | 3.3284 | 3.2648 | 3.2966 | 0.0636 | 2.7034 |
| 20 | 810 | 690 | 2.9085 | 2.8388 | 2.8737 | 0.0696 | 3.1263 |
| 21 | 300 | 320 | 2.4771 | 2.5051 | 2.4911 | 0.0280 | 3.5089 |
| 22 | 1390 | 1280 | 3.1430 | 3.1072 | 3.1251 | 0.0358 | 2.8749 |
| 23 | 1320 | 1340 | 3.1206 | 3.1271 | 3.1238 | 0.0065 | 2.8762 |
| 24 | 1460 | 1390 | 3.1644 | 3.1430 | 3.1537 | 0.0213 | 2.8463 |

Average 3.1402
Standard Dev 0.2650

APPARATUS FOR TESTING STERILIZATION METHODS AND MATERIALS

BACKGROUND OF THE INVENTION

1. Technical Field

This invention concerns sterilization and more particularly devices for testing hydrogen peroxide and related sterilization methods and materials.

2. Background Art

Many methods are used for sterilizing articles, including contacting them for a sufficient time with sterilizing liquids, sterilizing plasma, and/or sterilizing gases (e.g., steam). There obviously need to be methods for determining whether sterilization processes and materials (i.e., devices and other materials) are satisfactory (e.g., do they destroy a sufficient portion of the microorganisms likely to be present).

To help determine whether existing or proposed sterilization processes and devices are functioning or will function satisfactorily, biological indicators (e.g., biological test coupons) have been developed that contain precisely known amounts of specified microorganisms and provide precisely known resistance to sterilization. Chemical indicators have also been developed for the same purpose. Typically, one or more biological indicators are placed in a sterilization device to test (challenge, monitor, validate, etc.) the device and/or a process, the device is operated, and the biological indicators are thereafter removed and assayed to determine whether there was a sufficient reduction in the number of microorganisms. Chemical indicators are used in an analogous manner. Of course, a statistically sufficient sample of each such indicator must be tested to determine whether it is satisfactory for testing the sterilization device/process in question (e.g., is the indicator sensitive enough, does it provide accurate and consistent results).

A device for testing such indicators must be flexible (e.g., be able to be used throughout the ranges of interest for the parameters of interest), be able to rapidly provide uniform conditions throughout the chamber in which the biological or chemical indicators are exposed to (i.e., contacted with) the antimicrobial agent, and be precisely controllable with respect to all parameters (concentration of antimicrobial agent to which the indicator is exposed, exposure time of the indicator to the antimicrobial agent, temperature and pressure at which the exposure occurs, etc.). Such devices are sometimes referred to as "BIER" devices or units ("BIER" signifies "biological indicator evaluator resistometer"), even if they are used for testing chemical indicators.

Use of hydrogen peroxide vapor as the antimicrobial agent is relatively new as compared to use of steam and/or ethylene oxide as the antimicrobial agent. The gas phase containing vaporized hydrogen peroxide sterilant often also contains vaporized water and air. The water is initially present in such gas-phase sterilizing mixtures because hydrogen peroxide is readily commercially available as an aqueous liquid solution and it is more convenient to vaporize the entire solution to provide a hydrogen peroxide-water vapor rather than to try to separate the hydrogen peroxide from the water to obtain a water-free hydrogen peroxide vapor. The air is present in the gas-phase mixtures because it is an inexpensive and readily available gas that can be used as a diluent and/or to adjust the total pressure (a small amount of moisture will also be introduced into the initial gas-phase mixture by the air).

Use of hydrogen peroxide gas-phase sterilizing mixtures presents a number of problems, some of which are unique as compared to the use of older sterilants such as steam and ethylene oxide. For example, hydrogen peroxide immediately starts to decompose as soon as it is vaporized because the stabilizers that help retard or prevent decomposition of the hydrogen peroxide in aqueous solution do not function in the vapor phase (steam and ethylene oxide do not decompose). As a result, hydrogen peroxide vapor must be generated in "real time" (i.e., as it is needed or on demand), particularly for sterilization processes in which the hydrogen peroxide vapor concentration must be maintained above a predetermined minimum. Hydrogen peroxide has a substantially different vapor pressure curve than water (e.g., its normal boiling point is approximately 151° C. as compared to water's normal boiling point of 100° C.). Accordingly, differential evaporation (i.e., distillation) may occur when the aqueous solution of hydrogen peroxide is being vaporized. That makes producing a gas-phase mixture having a constant hydrogen peroxide concentration more difficult and it also increases the need for analytical methods that can rapidly and accurately indicate the hydrogen peroxide concentration (for monitoring and control). The condensation of hydrogen peroxide is influenced by the presence of water, and condensation of the hydrogen peroxide is something that someone operating a vapor-phase hydrogen peroxide sterilization process may wish to avoid. This reinforces the need to be able to carefully control sterilization parameters such as temperature and pressure. All of these factors increase the difficulty and complexity of operating hydrogen peroxide vapor-phase sterilization processes and the difficulty and complexity of adequately and properly testing biological and chemical indicators for such processes.

Documents concerning sterilization, hydrogen peroxide (including detection and determination of hydrogen peroxide and the production of hydrogen peroxide vapor), and related subject matter include U.S. Pat. Nos. Re. 33,007, 2,491,732, 3,851,436, 3,948,601, 4,169,123, 4,169,124, 4,230,663, 4,289,728, 4,296,068, 4,314,344, 4,321,232, 4,366,125, 4,401,755, 4,427,772, 4,437,567, 4,514,361, 4,525,265, 4,528,268, 4,642,165, 4,643,876, 4,671,936, 4,680,163, 4,707,334, 4,717,661, 4,743,537, 4,756,882, 4,795,707, 4,797,255, 4,828,797, 4,839,291, 4,843,867, 4,850,716, 4,863,688, 4,883,641, 4,885,253, 4,909,999, 4,914,034, 4,956,145, 4,992,247, 5,084,239, 5,114,670, 5,115,166, 5,139,957, 5,152,968, 5,167,927, 5,178,829, 5,180,553, 5,184,046, 5,186,893, 5,200,146, 5,244,629, 5,288,460, 5,317,896, 5,325,020, 5,364,590, 5,376,332, 5,413,758, 5,413,759, 5,413,760, 5,439,643, 5,445,792, 5,470,548, 5,472,664, 5,474,908, 5,482,684, 5,486,459, 5,492,672, 5,498,526, 5,503,807, 5,508,009, 5,512,244, 5,516,489, 5,516,648, 5,518,591, 5,525,295, 5,527,508, 5,534,221, 5,556,607, 5,593,649, 5,600,142, 5,603,895, 5,608,156, 5,620,656, 5,645,796, 5,650,693, 5,667,753, 5,674,450, 5,739,004, 5,750,184, 5,753,196, 5,770,393, 5,770,739, 5,779,973, 5,783,146, 5,788,925, 5,789,175, 5,792,435, 5,824,553, 5,830,409, 5,830,683, 5,843,374, 5,847,392, 5,847,393, 5,866,356, 5,870,885, 5,872,004, 5,872,359, 5,876,666, 5,892,229, 5,904,897, 5,911,950, 5,916,816, 5,923,432, 5,928,948, 5,938,917, 5,939,033, 5,942,408, 5,942,754, 5,972,199, 5,980,825, 5,989,852, 6,030,579, 6,036,918, 6,039,922, 6,056,918, 6,071,483, 6,075,246, 6,077,480, 6,094,523, 6,094,887, 6,096,265, 6,120,730, 6,132,680, 6,145,276, 6,149,878, 6,156,267, 6,174,502, 6,183,691, 6,189,368, and 6,203,756; European Patent Document No. EP 1,016,421; British Patent Document Nos. GB 1,582,060 and GB 2,089,213; Patent Cooperation Treaty Publication Nos. WO 00/57927, WO 00/65344, and WO 01/13964; Association for the Advancement of Medical Instrumentation, "Standard for BIER/Steam Vessels" (1981); Association for the Advancement of Medical Instrumentation, "BIER/Steam Vessels" (1992); Association for the Advancement of Medical Instrumentation, "Standard for BIER/EO Gas Vessels" (1982); Association for the Advancement of Medical Instrumentation, "BIER/EO Gas Vessels" (1992); Joslyn Valve Corp., "Biological Indicator Evaluator Resistometer (BIER)—Laboratory Test Systems For Steam And Ethylene Oxide," 4 pages (undated); U. S. Pharmacopoeia XXII, Official Monograph "Biological Indicators," pages 1625–1626 (undated); Herzberg, *Molecular Spectra and Molecular Structure*, II. Infrared and Raman Spectra of Polyatomic Molecules, page 532 (1945); Klapes et al., "Vapor-Phase Hydrogen Peroxide As A Surface Decontaminant And Sterilant," Applied and Environmental Microbiology, volume 56, number 2, pages 503–506 (1990); Skoog, Holler, Nieman, *Principles of Instrumental Analysis* (5th edition), pages 311–312 (1998); and Steinfeld, *Molecules and Radiation—An Introduction to Modem Molecular Spectroscopy*, page 229 (1974). (All of the foregoing documents, as well as all other documents cited or otherwise referenced herein, are incorporated herein in their entireties for all purposes.)

Biological indicators and chemical indicators are known. See, e.g., U.S. Pat. Nos. 4,401,755, 4,514,361, 4,528,268, 4,671,936, 4,717,661, 4,743,537, 4,828,797, 4,839,291, 4,883,641, 4,885,253, 4,914,034, 5,139,957, 5,486,459, 5,498,526, 5,516,648, 5,620,656, 5,739,004, 5,750,184, 5,770,393, 5,789,175, 5,824,553, 5,830,683, 5,866,356, 5,870,885, 5,872,004, 5,916,816, 5,989,852; Patent Cooperation Treaty Publication No. WO 00/65344; and U.S. Pharmacopoeia XXII, Official Monograph "Biological Indicators," pages 1625-1626 (undated). A "biological indicator" is defined in Association for the Advancement of Medical Instrumentation, "BIER/EO Gas Vessels" (1992), as a "[s]terilization process monitoring device consisting of a standardized, viable population of microorganisms (usually bacterial spores) known to be resistant to the mode of sterilization being monitored."

Devices for testing biological and/or chemical indicators and/or testing sterilization processes are known. See, e.g., U.S. Pat. Nos. 5,482,684 and 5,942,408; European Patent Document No. EP 1,016,421; Patent Cooperation Treaty Publication No. WO 01/13964; Association for the Advancement of Medical Instrumentation, "Standard for BIER/Steam Vessels" (1981); Association for the Advancement of Medical Instrumentation, "BIER/Steam Vessels" (1992); Association for the Advancement of Medical Instrumentation, "Standard for BIER/EO Gas Vessels" (1982); Association for the Advancement of Medical Instrumentation, "BIER/EO Gas Vessels" (1992); and Joslyn Valve Corp., "Biological Indicator Evaluator Resistometer (BIER)—Laboratory Test Systems For Steam And Ethylene Oxide," 4 pages (undated).

Association for the Advancement of Medical Instrumentation, "Standard for BIER/Steam Vessels" (1981), includes the following. "This standard establishes requirements for saturated steam vessels intended for the evaluation of the resistance performance of biological indicators (BIs)" (Section 1.1). "The preferred site for monitoring temperature is at the site of placement of the biological indicators" (Section 3.2.4.1). "The time to target temperature (e.g., 121±0.5° C., 204.8 kPa [29.7 psia] shall not exceed 10 seconds" and "[t]he time to exhaust sh be reproducible and shall not exceed 5 seconds" (Sections 3.2.4.2 and 3.2.4.3). "Critical operation of the saturated steam vessel requires that the pressure and temperature of the saturated steam be closely controlled . . ." (Section 4.1.1). "Pressure monitoring devices shall show that vessel pressure within ±3.45 kPa (±0.5 psi) of the saturated steam pressure" (Section 4.2.2). "Temperature control devices shall control the temperature of saturated steam to within ±0.5° C." (Section 4.3.1). See also Association for the Advancement of Medical Instrumentation, "BIER/Steam Vessels" (1992), a revision of the 1981 version.

Association for the Advancement of Medical Instrumentation, "Standard for BIER/EO Gas Vessels" (1982), includes the following. "This standard establishes requirements for ethylene oxide exposure vessels used to evaluate the resistance performance of biological indicators (BIs) that are intended for use in monitoring ethylene oxide sterilization cycles" (Section 1.1). "The time-to-gas concentration (at test temperatures and percent relative humidity) shall be reproducible at monitored site," "[t]he time-to-gas concentration for the exposed BI units shall not exceed 60 seconds," and "[t]he initial time-to-exhaust of the EO [ethylene oxide] from the exposure chamber shall be less than one minute and reproducible (±10 msec [sic]); after the end of the exposure period, items must be removed immediately from the test vessel" (Section 3.2.4). "Temperature control devices shall control the temperature to within ±1° C. at a specific monitored site," "[e]ach sterilizer shall be operated with a timer that has a precision of ±1.0 second," "[t]he quantity of gas admitted to the chamber must be controlled to ±5 percent of the gas concentration. . ." (Sections 4.3, 4.4, and 4.5). "There are two types of EO exposure systems. In the first, the test items (BIs) remain outside the exposure chamber until the conditions (temperature, percent relative humidity, and gas concentration) are stabilized; once the system is stable, the test items are exposed to the sterilizing environment by means of an insertion device or equivalent exposure device. In the second, the test items are placed within the exposure chamber; the system is brought to preexposure conditions (temperature and percent relative humidity stabilized); and then the vaporized gas is rapidly admitted into the exposure vessel. In both systems, timing of exposure begins when test units are exposed to the preselected EO conditions." (Section 5.1.1) See also Association for the Advancement of Medical Instrumentation, "BIER/EO Gas Vessels" (1992), a revision of the 1982 version. In the 1992 version, Section B.2 (entitled "Need For The Standard") states that "[t]he performance of biological indicators is critical to their acceptance as a means of monitoring ethylene oxide sterilization processes . . ." and that earlier studies "showed that a standard set of test conditions was required to meaningfully evaluate the performance of biological indicator lots."

U.S. Pat. No. 5,482,684 includes the following. "In addition to utility in monitoring the efficacy of a plasma sterilization cycle, the inventive vessel optionally is adapted to monitor a fluid sterilizing cycle (in addition to plasma), such as a cycle involving a fluid antimicrobial agent. Chemical indicators are useful in indicating such exposure to a fluid antimicrobial agent (or a component or reaction product of the agent), and Example 5 described hereinafter illustrates this aspect of the invention." (Column 5, lines 29–36) The antimicrobial agent may be hydrogen peroxide (column 6, lines 12–16; column 13, lines 37–45), and the plasma flow is continuous (column 8, lines 29–31). "Sterilizing chamber 14, in a limited sense, is a sterilizer of sorts; however, BIER vessels must perform so that the conditions to which the BIs are subjected are uniform. In addition to uniformity, another important aspect of the inventive BIER vessel is that the BIs being tested are exposed to sterilization conditions that reach a steady state in as short a time as practically possible. For example, in steam BIER vessels, the temperature must rise to the set point within ten seconds of the start of the test, while at the end of the test the steam must be vented away within five seconds. The required rise time in EtO vessels are somewhat slower." (Column 7, lines 24–35) "Chamber 14 has another outlet 42 whereby a monitor 52 monitors (or determines) the concentration of selected species in a plasma sterilizing cycle downstream of chamber 14. . . . The monitor 52 may include, for example, a mass spectrometer, a photometer, or a filter. The monitor 52 illustrated is a mass spectrometer, which is connected to the interior of a chamber 54, for example, to permit monitoring of the various combination of gases employed in the plasma." (Column 8, lines 40–53)

Sterilization devices and/or processes utilizing hydrogen peroxide are known (see, e.g., U.S. Pat. Nos. 4,169,123, 4,169,124, 4,230,663, 4,296,068, 4,366,125, 4,437,567, 4,643,876, 4,680,163, 4,707,334, 4,756,882, 4,797,255, 4,863,688, 4,909,999, 4,956,145, 4,992,247, 5,084,239, 5,114,670, 5,152,968, 5,244,629, 5,317,896, 5,413,758, 5,445,792, 5,472,664, 5,482,684, 5,492,672, 5,503,807, 5,508,009, 5,525,295, 5,527,508, 5,556,607, 5,593,649, 5,645,796, 5,667,753, 5,674,450, 5,770,739, 5,779,973, 5,783,146, 5,788,925, 5,792,435, 5,830,409, 5,843,374, 5,847,393, 5,876,666, 5,904,897, 5,911,950, 5,939,033, 5,980,825, 6,030,579, 6,039,922, 6,056,918, 6,077,480, 6,094,887, 6,096,265, 6,120,730, 6,132,680, 6,145,276, 6,149,878, 6,156,267, 6,174,502, 6,183,691, and 6,203,756; British Patent Document Nos. GB 1,582,060 and GB 2,089, 213; Klapes et al., "Vapor-Phase Hydrogen Peroxide As A Surface Decontaminant And Sterilant," Applied and Environmental Microbiology, volume 56, number 2, pages 503–506 (1990)), as are sterilization devices and processes using other modalities (e.g., plasma) with or without hydrogen peroxide (see, e.g., U.S. Pat. Nos. 3,851,436, 3,948,601, 4,321,232, 4,643,876, 4,756,882, 4,850,716, 5,084,239, 5,114,670, 5,115,166, 5,178,829, 5,180,553, 5,184,046, 5,186,893, 5,200,146, 5,244,629, 5,288,460, 5,317,896, 5,325,020, 5,364,590, 5,376,332, 5,413,758, 5,413,759, 5,413,760, 5,439,643, 5,470,548, 5,472,664, 5,512,244, 5,534,221, 5,593,649, 5,603,895, 5,645,796, 5,650,693, 5,753,196, 5,843,374, 5,876,666, 5,923,432, 5,928,948, 6,036,918, 6,071,483, 6,094,523, and 6,149,878; and Patent Cooperation Treaty Publication No. WO 00/57927).

It is known to break liquid hydrogen peroxide (e.g., in an aqueous solution) into particles and use them for, for example, sterilization, and it is known to vaporize liquid hydrogen peroxide (e.g., from such particles) and use the vapor for, for example, sterilization. See, e.g., U.S. Pat. Nos. Re. 33,007, 2,491,732, 4,296,068, 4,366,125, 4,642,165, 4,680,163, 4,707,334, 4,797,255, 4,863,688, 4,909,999, 4,992,247, 5,152,968, 5,525,295, 5,779,973, 6,077,480, and 6,096,265; British Patent Document Nos. GB 1,582,060 and GB 2,089,213; and Klapes et al., "Vapor-Phase Hydrogen Peroxide As A Surface Decontaminant And Sterilant," Applied and Environmental Microbiology, volume 56, number 2, pages 503–506 (1990).

There are many methods used to detect and/or determine the concentration of an analyte in a mixture or solution. See, for example, U.S. Pat. Nos. 4,314,344, 4,427,772, 4,525, 265, 4,795,707, 4,843,867, 5,139,957, 5,167,927, 5,474,908, 5,482,684, 5,516,489, 5,518,591, 5,600,142, 5,608,156, 5,788,925, 5,789,175, 5,847,392, 5,847,393, 5,872,359, 5,892,229, 5,938,917, 5,942,754, 5,972,199, 6,075,246, 6,156,267, and 6,189,368; and European Patent Document No. EP 1,016,421. It is known to detect and/or determine the concentration of a species in gas, vapor, or plasma. See, e.g., U.S. Pat. Nos. 4,314,344, 4,843,867, 5,139,957, 5,167,927, 5,482,684, 5,516,489, 5,600,142, 5,608,156, 5,788,925, 5,789,175, 5,847,392, 5,847,393, 5,872,359, 5,892,229, 6,075,246, 6,156,267, 6,189,368; and European Patent Document No. EP 1,016,421.

It is known to detect the presence of and/or determine the concentration of hydrogen peroxide (see, e.g., U.S. Pat. Nos. 4,427,772, 4,525,265, 4,795,707, 4,843,867, 5,139,957, 5,167,927, 5,474,908, 5,516,489, 5,518,591, 5,600,142, 5,608,156, 5,788,925, 5,789,175, 5,847,392, 5,847,393, 5,872,359, 5,892,229, 5,938,917, 5,942,754, 5,972,199, 6,156,267, and 6,189,368; and European Patent Application No. EP 1,016,421). It is known to detect and/or determine the concentration of hydrogen peroxide using spectrophotometry, e.g., using infrared or near-infrared energy. See, e.g., U.S. Pat. Nos. 5,600,142, 5,847,392, 5,847,393, 5,872, 359, 5,892,229, 5,942,754; and European Patent Document No. EP 1,016,421.

Attempts have been made to provide the functionalities required of a BIER unit for processes employing hydrogen peroxide vapor, but none of those attempts has succeeded in providing a device with the required accuracy, reproducibility, flexibility, speed, etc. For example, sealed packages containing articles have been placed in isolators containing hydrogen peroxide vapor and the packages quickly opened to allow hydrogen peroxide vapor to enter the packages to contact the articles; however, the accuracy and reproducibility were not satisfactory, in part because the rate of contact did not even approximate the required rapid commencement of contact, or the required constant hydrogen peroxide concentration throughout the entire contact period at the surface of the articles did not exist, etc.

As far as is known to applicants, there are no devices for accurately, reproducibly, and rapidly testing biological and/or chemical indicators for hydrogen peroxide sterilization (and as far as applicants know, there are no standards that anyone contemplating designing such a device could use). Thus, there is a need for such devices. Separate and apart from that, there is a need for devices that are sufficiently flexible, able to rapidly provide uniform conditions, precisely controllable, etc. for testing (including conducting research and development activities) processes and materials (i.e., devices and other materials) in the sterilization field involving hydrogen peroxide.

SUMMARY OF THE INVENTION

Apparatus and method that satisfy those needs and provide still other benefits that will be apparent to one skilled in the art have now been invented. Broadly, in a first aspect, the invention concerns an apparatus for testing one or more sterilization indicators by contacting them under controlled sterilization conditions with a flowing antimicrobial gas comprising hydrogen peroxide vapor, the apparatus comprising:

(a) a chamber in which the one or more sterilization indicators can be contacted with the flowing antimicrobial gas;

(b) means for rapidly placing the one or more sterilization indicators in the chamber while the flow of the antimicrobial gas in the chamber is substantially continuous and the concentration of hydrogen peroxide in the antimicrobial gas is substantially constant;

(c) means for continuing to flow the antimicrobial gas in the chamber to contact the one or more sterilization indicators from substantially the moment they are placed in the chamber, the contact being under substantially uniform conditions for the desired contact time, the flow of the antimicrobial gas during the contact being substantially continuous and the concentration of hydrogen peroxide in the antimicrobial gas during the contact being substantially constant; and (d) means for rapidly removing the one or more sterilization indicators from the chamber after the desired contact time of the one or more sterilization indicators with the antimicrobial gas has elapsed.

In a second aspect, the invention concerns the apparatus of the above-described first aspect of the invention further comprising antimicrobial gas generating means for providing the flowing antimicrobial gas comprising hydrogen peroxide vapor, the antimicrobial gas generating means comprising:

(a) a vaporization plenum having an inner surface;

(b) means for breaking a vaporizable liquid comprising hydrogen peroxide into fine particles and for flowing the fine particles in the vaporization plenum, the bulk flow of the fine particles flowing in the vaporization plenum being in a first direction;

(c) means for flowing a gas or vapor comprising a first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and (d) means for causing substantially all of the fine particles to vaporize in the flow of the first substance to produce a substantially continuous flow of a gas-phase mixture of the first substance and vaporized hydrogen peroxide of substantially constant hydrogen peroxide concentration as a function of time, the antimicrobial gas comprising the gas-phase mixture.

In a third aspect, the invention concerns a method for testing one or more sterilization indicators by contacting them under controlled sterilization conditions with a flowing antimicrobial gas comprising hydrogen peroxide vapor, the method comprising:

(a) rapidly placing the one or more sterilization indicators in the chamber of the apparatus of the above-described first aspect of the invention while the flow of the antimicrobial gas in the chamber is substantially continuous and the concentration of hydrogen peroxide in the antimicrobial gas is substantially constant;

(b) continuing to flow the antimicrobial gas in the chamber to contact the one or more sterilization indicators from substantially the moment they are placed in the chamber, the contact being under substantially uniform conditions for the desired contact time, the flow of the antimicrobial gas during the contact being substantially continuous and the concentration of hydrogen peroxide in the antimicrobial gas during the contact being substantially constant; and (c) rapidly removing the one or more sterilization indicators from the chamber after the desired contact time of the one or more sterilization indicators with the antimicrobial gas has elapsed.

In a fourth aspect, the invention concerns an apparatus for testing one or more sterilization indicators by contacting them under controlled sterilization conditions with a flowing antimicrobial gas comprising hydrogen peroxide vapor, the apparatus comprising:

(a) a chamber in which the one or more sterilization indicators can be contacted with the flowing antimicrobial gas;

(b) means for suddenly commencing and then continuing the contact of the flowing antimicrobial gas with the one or more sterilization indicators in the chamber under substantially uniform conditions for the desired contact time, the flow of the antimicrobial gas in the chamber during the contact being substantially continuous and the concentration of the hydrogen peroxide in the antimicrobial gas during the contact being substantially constant; and (c) means for suddenly halting the contact of the antimicrobial gas with the sterilization indicators after the desired contact time has elapsed.

In a fifth aspect, the invention concerns the apparatus of the above-described fourth aspect of the invention further comprising antimicrobial gas generating means for providing the flowing antimicrobial gas comprising hydrogen peroxide vapor, the antimicrobial gas generating means comprising:

(a) a vaporization plenum having an inner surface;

(b) means for breaking a vaporizable liquid comprising hydrogen peroxide into fine particles and for flowing the fine particles in the vaporization plenum, the bulk flow of the fine particles flowing in the vaporization plenum being in a first direction;

(c) means for flowing a gas or vapor comprising a first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and (d) means for causing substantially all of the fine particles to vaporize in the flow of the first substance to produce a substantially continuous flow of a gas-phase mixture of the first substance and vaporized hydrogen peroxide of substantially constant hydrogen peroxide concentration as a function of time, the antimicrobial gas comprising the gas-phase mixture.

In a sixth aspect, the invention concerns a method for testing one or more sterilization indicators by contacting them under controlled sterilization conditions with a flowing antimicrobial gas comprising hydrogen peroxide vapor, the method comprising:

(a) placing them in the chamber of the apparatus of the above-described fourth aspect of the invention (the antimicrobial gas may or may not be flowing at that time);

(b) suddenly commencing and then continuing the contact of the flowing antimicrobial gas with the one or more sterilization indicators in the chamber under substantially uniform conditions for the desired contact time, the flow of the antimicrobial gas in the chamber during the contact being substantially continuous and the concentration of the hydrogen peroxide in the antimicrobial gas during the contact being substantially constant; and (c) suddenly halting the contact of the antimicrobial gas with the sterilization indicators after the desired contact time has elapsed.

In a seventh aspect, the invention concerns an apparatus for testing sterilization processes that use a flowing antimicrobial gas comprising hydrogen peroxide vapor under controlled sterilization conditions, or for testing materials for such processes under controlled sterilization conditions, or for testing both such processes and such materials under controlled sterilization conditions, the materials comprising one or more articles, the apparatus comprising:

(a) a chamber in which the antimicrobial gas is flowed to provide contact of any one or more of the articles with the antimicrobial gas when articles are in the chamber;

(b) means for flowing the antimicrobial gas in the chamber to contact any such one or more articles under substantially uniform conditions for the desired time, the flow of the antimicrobial gas in the chamber during the desired time being substantially continuous and the concentration of the hydrogen peroxide in the antimicrobial gas during the desired time being substantially constant; and (c) means for halting the flow of the flowing antimicrobial gas after the desired time has elapsed.

In an eighth aspect, the invention concerns the apparatus of the above-described seventh aspect of the invention further comprising antimicrobial gas generating means for providing the flowing antimicrobial gas comprising hydrogen peroxide vapor, the antimicrobial gas generating means comprising:

(a) a vaporization plenum having an inner surface;

(b) means for breaking a vaporizable liquid comprising hydrogen peroxide into fine particles and for flowing the fine particles in the vaporization plenum, the bulk flow of the fine particles flowing in the vaporization plenum being in a first direction;

(c) means for flowing a gas or vapor comprising a first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and (d) means for causing substantially all of the fine particles to vaporize in the flow of the first substance to produce a substantially continuous flow of a gas-phase mixture of the first substance and vaporized hydrogen peroxide of substantially constant hydrogen peroxide concentration as a function of time, the antimicrobial gas comprising the gas-phase mixture.

In a ninth aspect, the invention concerns a method for testing sterilization processes that use a flowing antimicrobial gas comprising hydrogen peroxide vapor, or for testing materials for such processes, or for testing both such processes and such materials, the materials comprising one or more articles, the method comprising:

(a) flowing the antimicrobial gas to provide contact of any one or more articles with the antimicrobial gas when the articles are in the chamber of the apparatus of the above-described seventh aspect of the invention;

(b) flowing the antimicrobial gas in the chamber to contact any such one or more articles under substantially uniform conditions for the desired time, the flow of the antimicrobial gas in the chamber during the desired time being substantially continuous and the concentration of the hydrogen peroxide in the antimicrobial gas during the desired time being substantially constant; and (c) halting the flow of antimicrobial gas after the desired time has elapsed.

In some preferred embodiments: the apparatus further comprises means for pre-treating the one or more sterilization indicators or other articles (e.g., drying to remove moisture to retard hydrogen peroxide condensation from the gas-phase mixture, heating to a temperature above the dew point of the antimicrobial gas, cooling) before their contact with the antimicrobial gas has commenced; and/or the apparatus further comprises means for post-treating the one or more sterilization indicators or other articles after they have been removed from the chamber (e.g., degassing to remove any residual antimicrobial gas from them); and/or the apparatus further comprises means for pre-treating and means for post-treating; the means for pre-treating and the means for post-treating comprise at least some of the same members; and/or the apparatus further comprises an antechamber and the means for pre-Treating and the means for post-treating each comprise the antechamber; and/or the apparatus further comprises a movable member and means for moving the movable member from the chamber to the antechamber and from the antechamber to the chamber; and/or the means for rapidly placing the one or more sterilization indicators in the chamber and the means for rapidly removing the one or more sterilization indicators from the chamber after the desired contact time has elapsed are the same and each comprises the movable member; and/or the apparatus further comprises means to maintain the one or more sterilization indicators in a predefined volume in the chamber; and/or the apparatus further comprises means to flow substantially all of the antimicrobial gas flowing into the chamber through the predefined volume; and/or the apparatus further comprises means for monitoring the hydrogen peroxide concentration of the antimicrobial gas; and/or the apparatus further comprises means for maintaining the contact of the antimicrobial gas with the sterilization indicators at a desired temperature; and/or the antimicrobial gas generating means is oriented so that the first direction is up and substantially vertical; and/or the antimicrobial gas generating means further comprises means for flowing substantially all of the first substance fed to the vaporization plenum between the inner surface of the vaporization plenum and substantially all of the fine particles to create the curtain of first substance.

This invention provides apparatus and method for testing one or more sterilization indicators or other articles by contacting them under controlled sterilization conditions with a flowing antimicrobial gas containing hydrogen peroxide vapor. This invention also provides apparatus and method for testing sterilization processes that use a flowing antimicrobial gas containing hydrogen peroxide vapor under controlled sterilization conditions, or for testing materials for such processes under controlled sterilization conditions, or for testing both such processes and such materials under controlled sterilization conditions. In all cases, the invention can provide an essentially square-wave contact of the sterilization indicators or other articles with the antimicrobial gas (i.e., short rise time to reach full concentration of the antimicrobial gas in contact with the sterilization indicators or other articles and short fall time to remove all of the antimicrobial gas from contact with the sterilization indicators or other articles). The invention can also make use of a novel way of generating a substantially constant flow of antimicrobial gas of substantially constant hydrogen peroxide concentration. The invention also preferably utilizes a novel method employing a spectrophotometric device to determine a monotonic functional relationship between concentration and integrated absorbance to monitor hydrogen peroxide concentration. The relationship so determined also allows calibration of a hydrogen peroxide detection device substantially less expensive than the spectrophotometric device. In all cases, the invention provides substantially uniform conditions for the contact of the antimicrobial gas with the sterilization indicators or other articles. This invention is believed to provide the first devices that are sufficiently flexible, that are able to rapidly provide uniform conditions, that are precisely controllable, etc. for testing (including conducting research and development activities) for processes and materials (i.e., articles and other materials) in the sterilization field involving hydrogen peroxide (e.g., hydrogen peroxide BIER units). This invention has still other features and benefits that will be apparent to one skilled in the art.

BRIEF DESCRIPTION OF THE DRAWINGS

To facilitate further description of the invention, the following drawings are provided in which.

Figure 1:
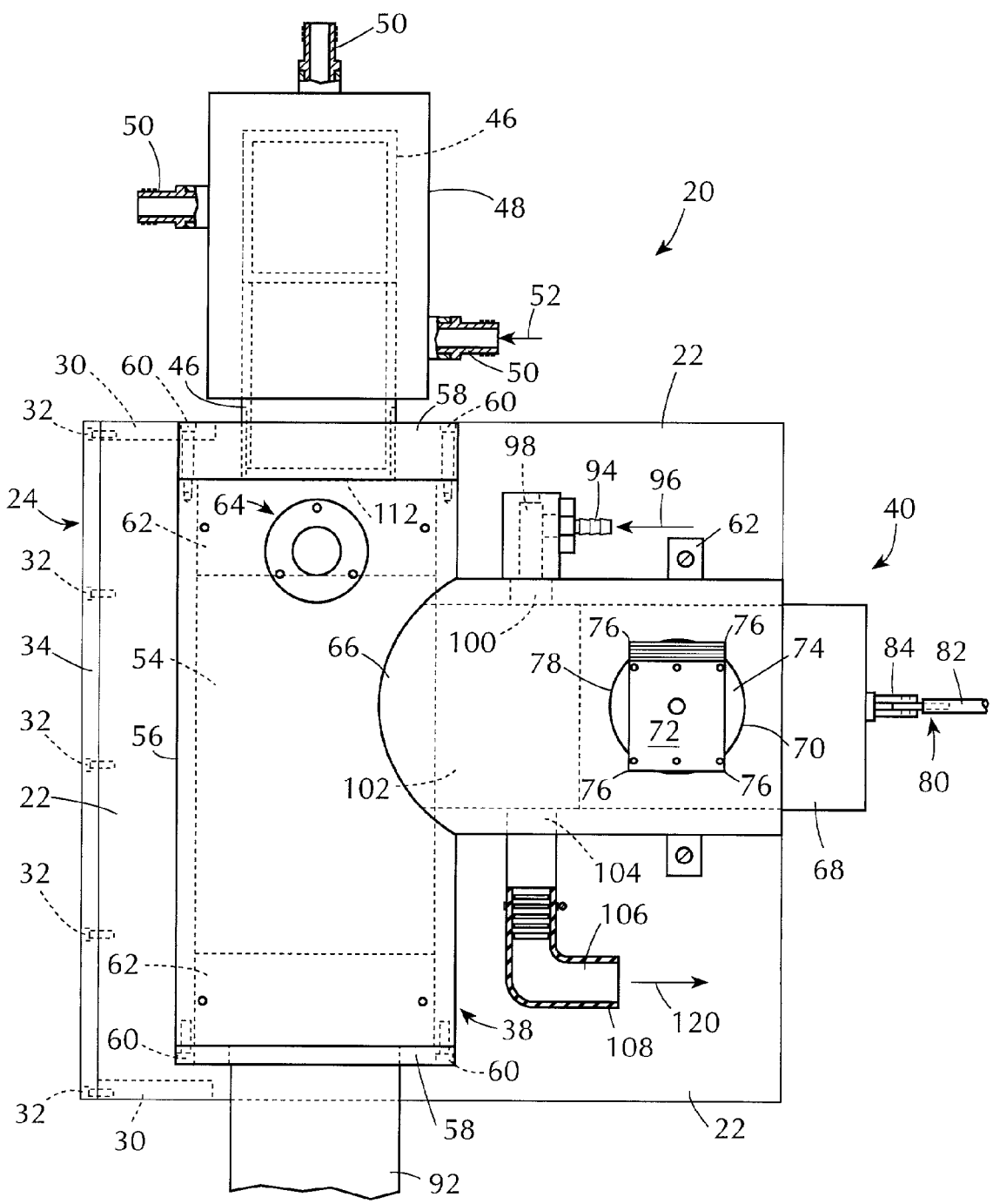
FIG. 1 is a plan view of a device in accordance with this invention for providing substantially uniform contact of an antimicrobial gas containing hydrogen peroxide with sterilization materials (e.g., biological indicators)

These drawings are provided for illustrative purposes only and should not be used to unduly limit the scope of the invention.

DETAILED DESCRIPTION OF THE INVENTION

The apparatus and method of the present invention can be used for testing one or more sterilization indicators by contacting them under controlled sterilization conditions with a flowing antimicrobial gas containing (i.e., comprising) hydrogen peroxide vapor. The apparatus and method of this invention can also be used for testing sterilization processes that use a flowing antimicrobial gas containing (i.e., comprising) hydrogen peroxide vapor under controlled sterilization conditions, or for testing materials for such processes under controlled sterilization conditions, or for testing both such processes and such materials under controlled sterilization conditions.

The invention can make use of novel method and apparatus for generating a substantially constant flow of antimicrobial gas of substantially constant hydrogen peroxide concentration. That method and apparatus are the subject of a patent application being filed concurrently herewith entitled "Production of Hydrogen Peroxide Vapor-Air Mixtures," naming Davoud Khorzad, Robert J. Thrash, Jimmy Fisher, and Thomas F. Cullen as inventors, and assigned to Pharmaceutical Systems, Inc. Ser. No. 09/901,337. That application is incorporated herein in its entirety for all purposes.

The invention can also make use of a novel method employing spectroscopy to determine a monotonic functional relationship between concentration and integrated absorbance to monitor hydrogen peroxide concentration. The relationship so determined also allows calibration of a detection device substantially less expensive than a spectrophotometric device (such as the above-described Analect FTIR device), and that less expensive detection device (e.g., the above-described Drager device) may then be used as part of an apparatus of this invention. The novel method employing spectroscopy is the subject of a patent application being filed concurrently herewith entitled "Spectrophotometric Determination Of Gas Phase Compositions," naming Robert J. Thrash, Thomas F. Cullen, Davoud Khorzad, and Jimmy Fisher as inventors, and assigned to Pharmaceutical Systems, Inc. Ser. No. 09/901,221. That application is incorporated herein in its entirety for all purposes.

The apparatus and method of the present invention allow accurate, reproducible, and rapid testing of "sterilization indicators," which should be broadly understood and includes biological indicators, chemical indicators, and all other physical and chemical indicators of degrees of sterility for antimicrobial gas containing hydrogen peroxide. The apparatus and method of the present invention also allow accurate, reproducible, and rapid testing of processes and materials with antimicrobial gas containing hydrogen peroxide. "Testing" should be broadly understood and includes all activities that can be conducted using this apparatus, including, for example, validating, challenging, and monitoring. "Materials" should be broadly understood and includes all tangible things that can be tested using this apparatus, including biological indicators, chemical indicators, and all other articles that can be tested (e.g., devices and other articles that can be subjected to antimicrobial gas).

The apparatus of this invention is flexible (e.g., it can be used throughout the ranges of interest for the parameters of interest, such as temperature, pressure, contact time, hydrogen peroxide concentration in the antimicrobial gas, and antimicrobial gas flowrates), can rapidly provide uniform conditions for contact of the materials with the antimicrobial gas, and is precisely controllable. The invention can provide an essentially square-wave contact of the sterilization indicators or other articles with the antimicrobial gas (i.e., a short rise time to reach full concentration of the antimicrobial gas in contact with the sterilization indicators or other materials and a short fall time to remove all of the antimicrobial gas from contact with the sterilization indicators or other materials).

To achieve the desired square-wave contact, a substantially continuous flow of antimicrobial gas of substantially constant hydrogen peroxide concentration is rapidly or suddenly brought into contact with the materials in question (e.g., biological indicators). That may be accomplished in any feasible manner. For example, the materials to be contacted with the antimicrobial gas may be placed in a chamber and the flow of antimicrobial gas may be rapidly or suddenly diverted into the chamber to commence its contact with the materials. Alternatively, the antimicrobial gas may already be flowing in the chamber and the materials may be rapidly or suddenly moved into the flow of gas in the chamber. Any other scheme that allow the benefits of this invention to be achieved may be used.

As used herein, words "rapidly," "suddenly," and the like with respect to an action should be understood to mean that from start to finish, the action requires or lasts not more than 120 seconds, desirably not more than 90 seconds, more desirably not more than 60 seconds, most desirably not more than 45 seconds, preferably not more than 30 seconds, more preferably not more than 15 seconds, most preferably not more than 10 seconds, and in some cases even as little as 5 seconds or less. Thus, for example, "rapidly placing the one or more sterilization indicators in the [exposure] chamber" most preferably requires not more than 10 seconds but may take substantially less time, depending on the size of the apparatus etc. Similarly, "suddenly commencing . . . the contact of the flowing antimicrobial gas with the one or more sterilization indicators" most preferably requires not more than 10 seconds but may take substantially less time, depending on the size of the apparatus, the flowrate of the gas, etc. Similarly, "rapidly removing the one or more sterilization indicators from the chamber" most preferably requires not more than 10 seconds but may take substantially less time, depending on the size of the apparatus etc.

In some embodiment, the antimicrobial gas is flowed in the chamber to contact the one or more sterilization indicators or other materials from substantially the moment they are placed in the chamber. In this context, "from substantially the moment" means that the contact commences within not more than 120 seconds, desirably within not more than 90 seconds, more desirably within not more than 60 seconds, most desirably within not more than 45 seconds, preferably within not more than 30 seconds, more preferably within not more than 15 seconds, most preferably within not more than 10 seconds, and in some cases within as little as 5 seconds, from time the sterilization indicators or other materials are placed in the chamber.

The present invention provides substantially uniform conditions during the contact period of the antimicrobial gas with the sterilization indicators or other materials. The term "substantially uniform conditions" and the like mean that over the time period during which contact occurs, each of the key parameters (temperature of the contact in the exposure chamber, flow of the antimicrobial gas onto the materials in question in the exposure chamber, and hydrogen peroxide concentration of the antimicrobial gas flowing onto those materials) does not vary from its mean time-average value for the period by more than 25% of the mean time-average value, desirably by not more than 20%, more desirably by not more than 15%, most desirably by not more than 10%, preferably by not more than 7.5%, more preferably by not more than 5%, most preferably by not more than 2.5%, and in some cases by not more than 1.5%.

Hydrogen peroxide is typically sold in aqueous solution, for example, at concentrations of 3% w/w, 10% w/w, 30% w/w, 35% w/w, and higher (e.g., 70% w/w), and the manufacturers generally add proprietary stabilizers (e.g., chelants/sequestrants such as organic and inorganic phosphates and/or stannates and/or silicates) to the liquid solution to minimize decomposition. Unfortunately, these stabilizers do not function in the vapor phase and once an aqueous liquid solution of hydrogen peroxide is vaporized, as it typically is in hydrogen peroxide vapor phase sterilizing processes, decomposition of the hydrogen peroxide immediately begins and continues unabated.

Because the half-life of hydrogen peroxide in the gas phase at room temperature is approximately 10–15 minutes, which may be approximately equal to the typical contact time for an article with hydrogen peroxide-containing antimicrobial gas, it would be almost impossible to maintain substantially uniform conditions with respect to the desired hydrogen peroxide concentration of the antimicrobial gas contacting the sterilization indicators or other articles if fresh antimicrobial gas containing the hydrogen peroxide at the desired concentration were not continuously flowed into the exposure chamber. Thus, the method and apparatus of this invention make use of flowing antimicrobial gas comprising (i.e., containing) hydrogen peroxide.

To help make the conditions of the contact substantially uniform in the chamber, the flow of antimicrobial gas into and through the chamber should be substantially continuous and the concentration of the hydrogen peroxide in the antimicrobial gas should be substantially constant. Such a flow into the chamber can be provided using the method and apparatus of the above-referenced patent application entitled "Production of Hydrogen Peroxide Vapor-Air Mixtures," naming Davoud Khorzad, Robert J. Thrash, Jimmy Fisher, and Thomas F. Cullen as inventors, and assigned to Pharmaceutical Systems, Inc. Ser. No. 09/901,337.

By "substantially continuous" is meant that the flow satisfies at least one of the following criteria: (a) over the time period of interest, the minimum flow in the exposure chamber is at least 50% (desirably at least 60%, more desirably at least 70%, most desirably at least 75%, preferably at least 80%, more preferably at least 85%, and most preferably at least 90%) of the maximum flow in the exposure chamber, or (b) over the time period of interest, each of the minimum and maximum flows in the exposure chamber differ from the time-average flow in the exposure chamber by no more than 30% (desirably by no more than 25%, more desirably by no more than 20%, most desirably by no more than 15%, preferably by no more than 12.5%, more preferably by no more than 10%, and most preferably by no more than 7.5%) of the time-average flow in the exposure chamber, or (c) over the time period of interest, the time-average flow for each successive minute long period is at least 60% (desirably at least 70%, more desirably at least 75%, most desirably at least 80%, preferably at least 85%, more preferably at least 90%, and most preferably at least 95%) of the time-average flow in the exposure chamber. With respect to the hydrogen peroxide concentration being substantially constant in the antimicrobial gas in the exposure chamber, "substantially constant" means that over the time period of interest, no concentration within that time period varies from the mean time-averaged hydrogen peroxide concentration over that period by more than plus or minus 15%, desirably by no more than plus or minus 10%, more desirably by no more than plus or minus 8%, most desirably by no more than plus or minus 6%, preferably by no more than plus or minus 4%, more preferably by no more than plus or minus 2%, and most preferably by no more than plus or minus 1%. In other words, none of the instantaneously measured concentrations of the hydrogen peroxide deviates from the average by more than plus or minus 15% of the average value, desirably by no more than plus or minus 10% of the average value, more desirably by no more than plus or minus 8%, etc.

In the chamber, the flow of the antimicrobial gas should be well-mixed to help prevent variations such as temperature variations from micro-region to micro-region. For example, temperature variations might encourage variations in concentration from micro-region to micro-region. One possible cause is that a cooler temperature might tend to encourage condensation (which would reduce the concentration of hydrogen peroxide in that micro-region), depending on how close the antimicrobial gas was to the dew point, and a warmer temperature might tend to encourage faster decomposition of the hydrogen peroxide (which might also reduce the concentration of hydrogen peroxide in that micro-region). Depending on the particular antimicrobial agent, its presence as a liquid on the surface of a biological indicator or other article might tend to reduce the antimicrobial activity of the agent in the gas phase by interfering with the vapor-phase contact of the agent with the article. In any case, turbulent flow of the antimicrobial gas in the chamber will often be preferred (because it encourages good mixing), although with certain designs, laminar flow may be preferred. Another preferred flow pattern (regardless of whether the flow is turbulent or laminar) is to have substantially all the antimicrobial gas flow through the imaginary "predefined volume" occupied by the sterilization indicator or other article being contacted with the antimicrobial gas. In this context, "flow substantially all of the antimicrobial gas flowing into the chamber through the predefined volume" and similar terms mean that at least 70%, desirably at least 75%, more desirably at least 80%, most desirably at least 80%, preferably at least 85%, more preferably at least 90%, most preferably at least 95%, and in some cases 100% of the antimicrobial gas flowing into the chamber flows through the predefined volume in which the sterilization indicators or other articles are maintained in the chamber during contact.

The pressure inside the exposure chamber can be any pressure that allows the benefits of this invention to be achieved. The pressure in the exposure chamber will generally be at least a few torr and desirably at least about 200 torr, more desirably at least 300 torr, most desirably at least 400 torr, preferably at least 500 torr, more preferably at least 600 torr, most preferably at least 700 torr, and even above 760 torr (atmospheric pressure). The pressure will typically not be more than about 2 atmospheres, although for some designs, higher pressure can be used.

The contact temperature inside the main chamber can be any temperature that allows the benefits of this invention to be achieved. A desirable temperature range is 0 to 85° C., in other words, a "cool" contact temperature.

Because temperature is a key parameter, various means may be provided to help insure that the contact of the antimicrobial gas with the sterilization indicators or other articles occurs at the desired temperature. Such means include temperature regulation of the gas flow entering the chamber. The temperature of that entering gas flow is determined by the temperature at which the antimicrobial gas leaves the gas generation means and the temperature to which the gas is heated or cooled by any subsequent heating or cooling step. The means to help insure that the contact occurs at the desired temperature may also include means for adjusting the temperature of the sterilization indicators or other articles before they contact the antimicrobial gas. Thus, the articles may be preheated or precooled. The means to help insure that the contact occurs at the desired temperature may also include means for adjusting the temperature of the chamber, such as means for heating the chamber and/or means for cooling the chamber during the contact of the antimicrobial gas with the articles. Any such means may be used (e.g., electrical heating tape, hot oil bath, hot water bath, cooling water bath, cooling coils). These means may be located outside the members defining the chamber (e.g., the walls), inside the members themselves (e.g., the walls) of the chamber, and/or inside the chamber itself.

Any suitable pre-treatment of the sterilization indicator or other materials may be conducted prior to the time of contact of the materials with the flowing hydrogen peroxide-containing antimicrobial gas. The pre-treatment may occur in the same chamber where exposure to the antimicrobial gas containing the hydrogen peroxide is to occur or it may occur in a different chamber. "Pre-treatment" should be understood to include heating, cooling, drying, exposing to other antimicrobial agents, etc. One desirable pre-treatment may be pre-heating to raise the temperature of the materials above the dew point of the antimicrobial gas prior to their contact with the antimicrobial gas to prevent condensation (e.g., of the hydrogen peroxide). Drying (e.g., by flowing dry gas onto to materials) may be a desirable pre-treatment to reduce the water on and immediately around the materials prior to contact with the antimicrobial gas because the presence of water may cause the hydrogen peroxide to condense out of the gas-phase.

Any suitable post-treatment of the sterilization indicator or other materials may be conducted subsequent to the time of contact of the materials with the flowing hydrogen peroxide-containing antimicrobial gas. The post-treatment may occur in the same chamber where exposure to the antimicrobial gas containing the hydrogen peroxide has occurred or it may occur in a different chamber. The same chamber (e.g., an antechamber to the exposure chamber) and other means used for any pre-treatment may also be used for any post-treatment. "Post-treatment" should be understood to include heating, cooling, freezing, drying, exposing to other antimicrobial agents, etc. A typical post-treatment is degassing to remove any residual antimicrobial gas that may remain on the materials that were exposed to the antimicrobial gas after the flow of the flowing antimicrobial gas has halted. Degassing may be carried out by flowing gas not containing hydrogen peroxide onto the materials.

If rapid or sudden contact of the flowing antimicrobial gas with the sterilization indicators or other materials is to be made by rapidly moving the materials into the flowing gas stream, any means for moving the materials may be used. For example, the materials may be placed in or on or otherwise associated with a moveable member and the movable member rapidly moved into the exposure chamber. The antimicrobial gas may already be flowing in the chamber or the gas flow may be rapidly started as soon as the articles are in the chamber.

If rapid or sudden contact of the flowing antimicrobial gas with the sterilization indicators or other materials is to be made by placing the materials in a given position and then rapidly or suddenly diverting or flowing the gas stream onto them, any means for placing the materials may be used and any means for suddenly diverting or flowing the gas stream onto the materials may be used. For example, the materials may be placed in or on or otherwise associated with a moveable member and the movable member moved into the exposure chamber. The flow of the antimicrobial gas may then be suddenly started or it may already be flowing along a different path and then suddenly diverted into the chamber onto the materials to be contacted.

The antimicrobial gas used herein contains hydrogen peroxide. The gas may contain any other one or more gases or one or more vapors that do not prevent the advantages of this invention from being achieved. Accordingly, the antimicrobial gas may also contain air, water vapor, peroxidants (e.g., peracids, peroxides) and/or other sterilants or antimicrobial gases or vapors. As noted above, hydrogen peroxide is typically sold in aqueous solution. Thus, the antimicrobial gas used herein will typically contain (but need not contain) water vapor. A preferred antimicrobial gas used herein also contains air (in addition to the hydrogen peroxide vapor and water vapor) and is made using the method and apparatus of the above-referenced patent application entitled "Production of Hydrogen Peroxide Vapor-Air Mixtures," naming Davoud Khorzad, Robert J. Thrash, Jimmy Fisher, and Thomas F. Cullen as inventors, and assigned to Pharmaceutical Systems, Inc. Ser. No. 09/901,337.

With this background, we turn to the accompanying drawings, which show an apparatus of this invention.

Figure 2:
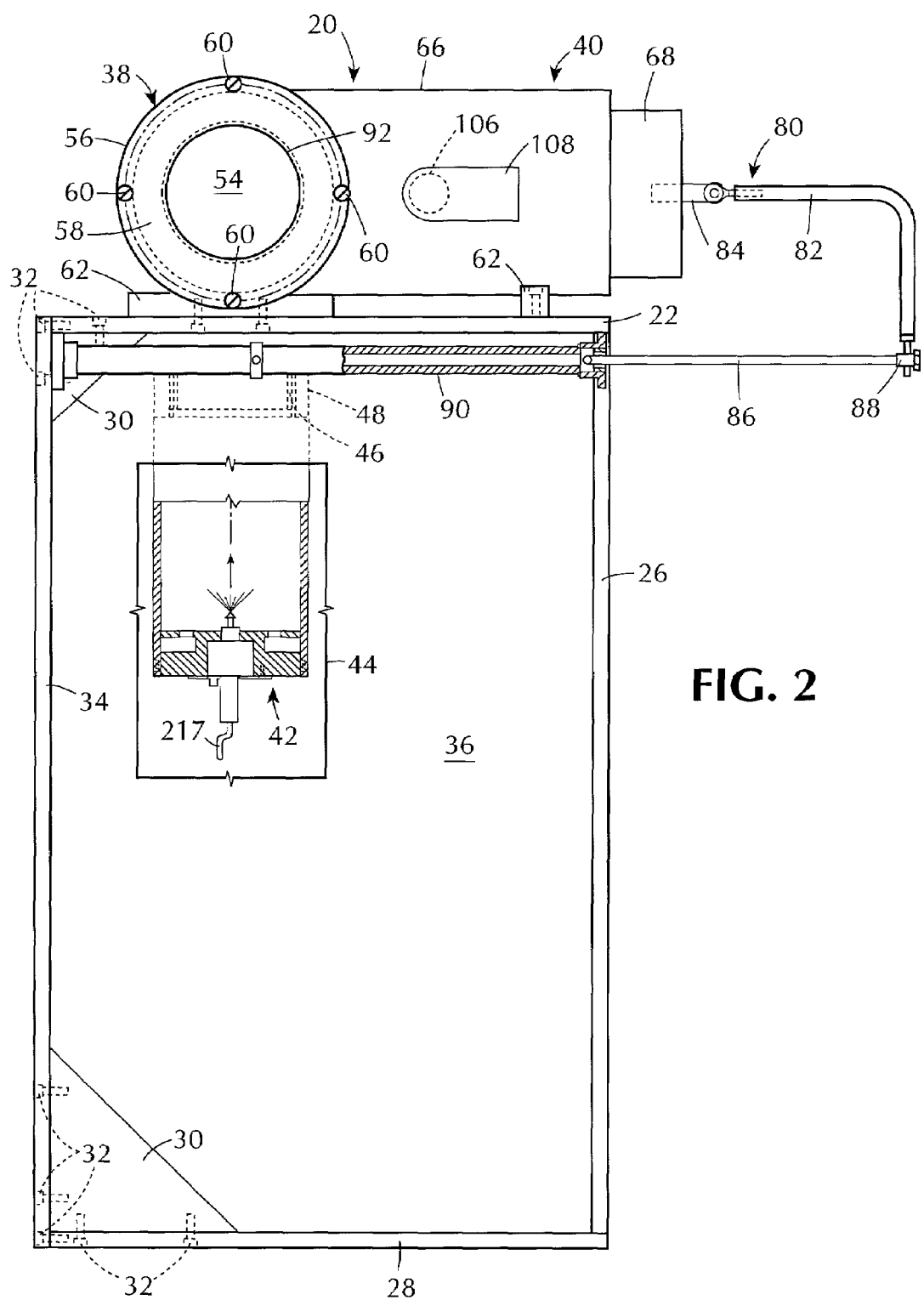
FIG. 2 is a front view of the device of FIG. 1.
Figure 3:
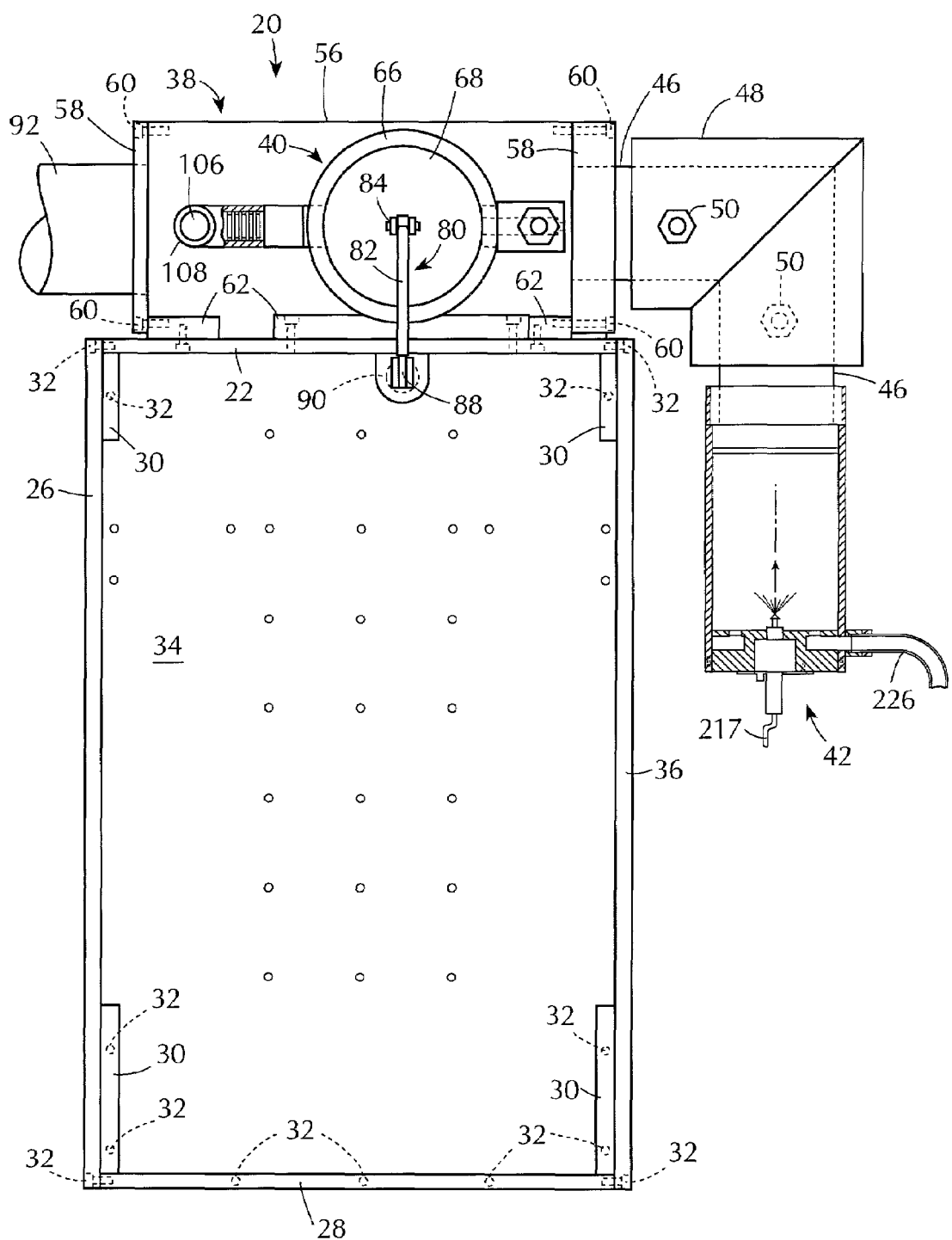
FIG. 3 is a side view of the device of FIG. 1.

FIGS. 1, 2, and 3 show, respectively, top, front, and right-side views of BIER/testing apparatus 20. Shuttle assembly 40 is connected to exposure chamber assembly 38 at a right angle, and both rest on several supporting blocks 62, which in turn rest on top panel 22. Top panel 22 is connected to frame 24, which comprises vertical frame members 26, bottom frame members 28, side panel 34, back panel 36, and reinforcing blocks 30, all held together by screws 32. Antimicrobial gas generator 42 is located at the back of apparatus 20 (visible through imaginary cut-out 44 in FIG. 2, as well as in FIG. 3). Aqueous hydrogen peroxide solution flows through inlet tube 217 into the gas generator and warm dry air enters through air feed tube 226. The antimicrobial gas containing hydrogen peroxide flows up out of generator 42, through duct 46, and through opening 112 in end plate 58, which plate is connected by screws 60 to the back end of pipe 56 in which exposure (main) chamber 54 is located. Antimicrobial gas leaving chamber 54 flows through outlet piping 92, which is connected to front plate 58, also fastened to pipe 56 by screws 60.

Exposure (main) chamber 54 is contained within pipe 56, which is 7.5 inches outer diameter (19 centimeters) and 6.5 inches inner diameter (16.5 centimeters). Cylindrical chamber 54 is bounded at its two circular ends by plates 58, the inner surfaces of which are 15 inches (38.1 centimeters) apart.

Figure 9:
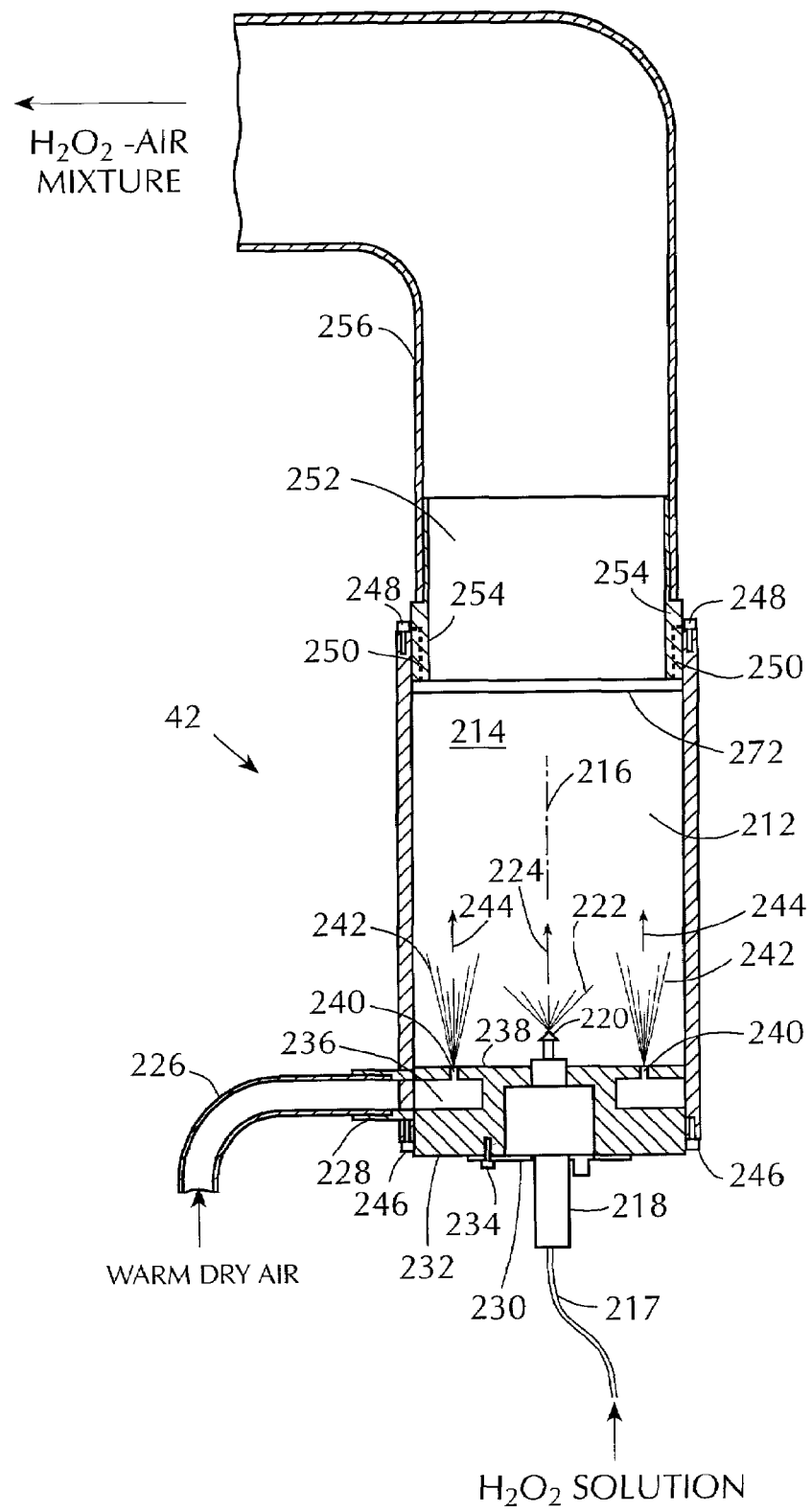
FIG. 9 is a side sectional view of a first apparatus that can be used as part of this invention for producing hydrogen peroxide vapor-air mixtures of substantially constant hydrogen peroxide concentration at substantially continuous flow rates.

Although duct 46 is shown as having squared corners, a device of this invention that was built used a curved bend (as in FIG. 9). The square corners may help increase the turbulence of the flow, which, as noted above, may be desirable in some cases. Also, although temperature moderator 48 (i.e., a heating or cooling jacket with nipples 50 for the flow of heating or cooling fluid, as indicated by in-flow arrow 52) is depicted in the figures, a device of this invention that was built did not have a temperature moderator. It is believed that temperature moderator 48 may be desirable for some designs.

Drager device assembly 64 (also see detail FIG. 8) sits atop pipe 56. That Drager device is one described above (Drager Sensor $H_2O_2$ HC, Model 6809070, manufactured by Dragerwerk AG and marketed by Draeger Safety, Inc.) and is oriented to measure the hydrogen peroxide concentration of the antimicrobial gas before it contacts the articles to be treated. The Drager unit may be placed at any location that allows the benefits of this invention to be achieved.

Shuttle assembly 40 comprises pipe 66, which is 6.75 inches outer diameter (17.1 centimeters) and 5.5 inches inner diameter (14 centimeters). Shuttle 68 is a solid cylindrical block (having certain concavities and passageway to be described below) whose length is 7.5 inches (19.1 centimeters) and whose outer diameter is essentially the same as the inner diameter of pipe 66, thereby providing a sufficiently tight fit to retard the flow of gas between the pipe and the shuttle. When the pressure inside the device is approximately atmospheric, the tight fit between shuttle 68 and pipe 66 is sufficient to prevent any significant flow in either direction; however, if the pressure inside the device is substantially higher or lower than atmospheric, it may be desirable to include O-rings or other sealing means in the device to prevent the antimicrobial gas from leaving the chamber or to prevent air from flowing into the chamber.

Figure 4:
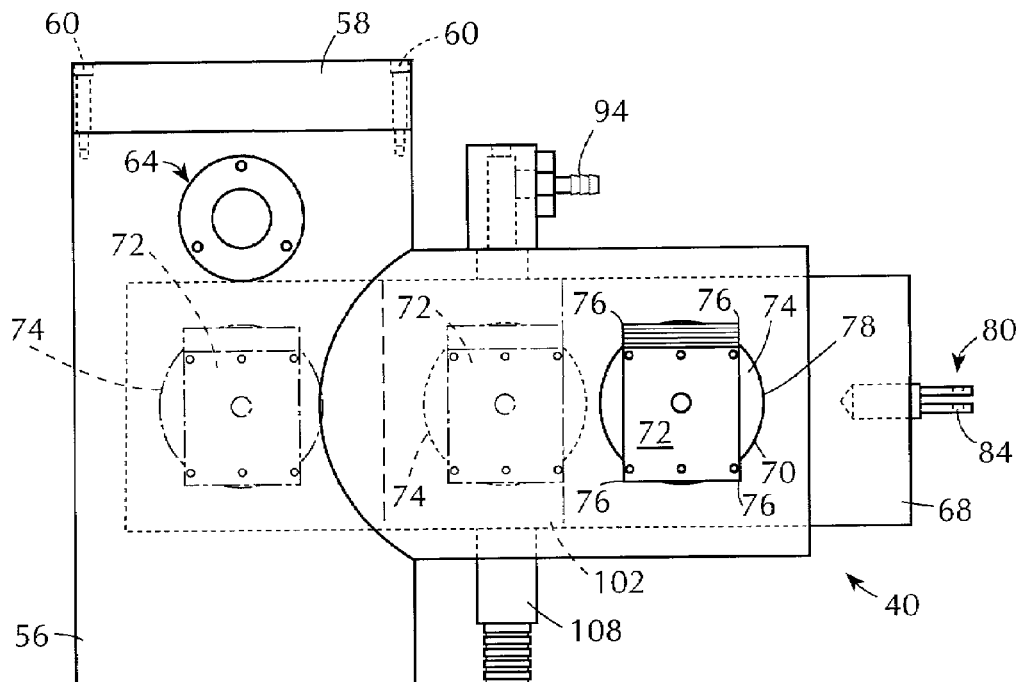
FIG. 4 is a partial plan view of the device of FIG. 1 showing the three different positions for the shuttle mechanism that is used to move a sample holder from one of those positions to another.
Figure 5:
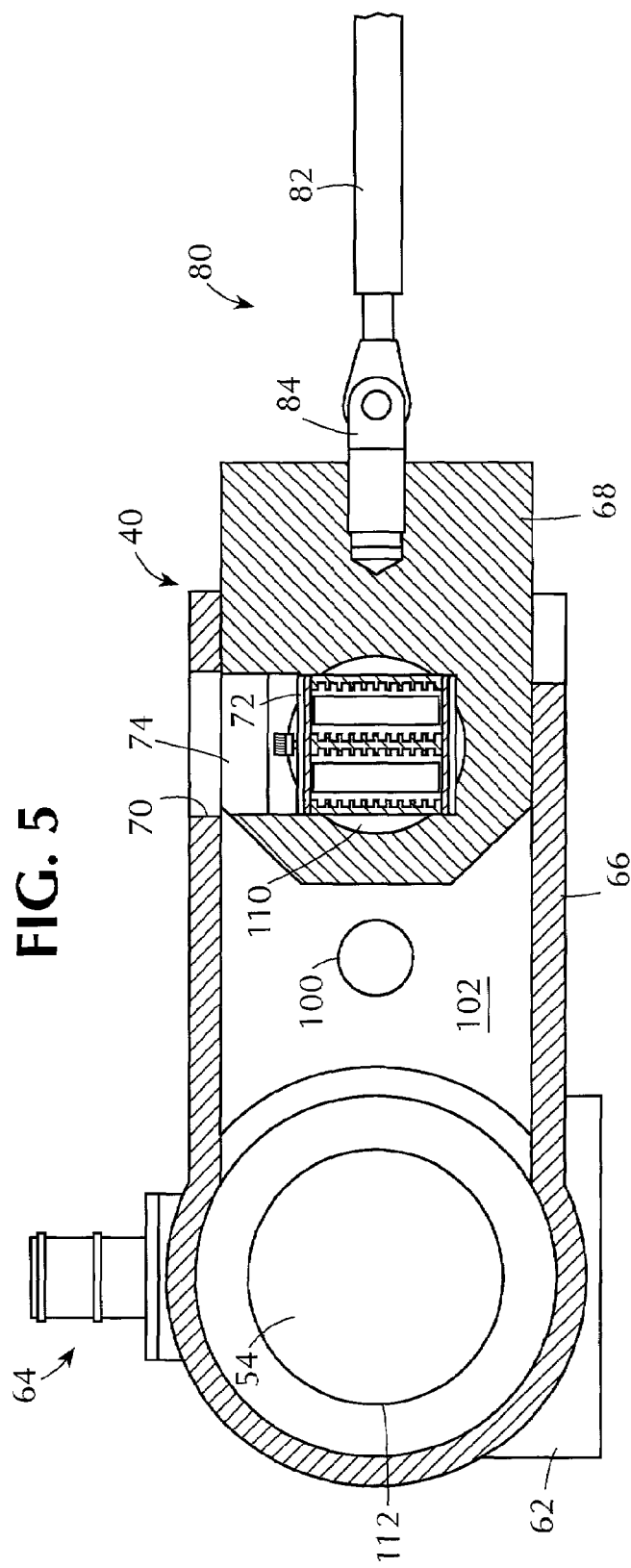
FIG. 5 is a cross-sectional front view showing the shuttle and sample holder in the first (load) position.
Figure 6:
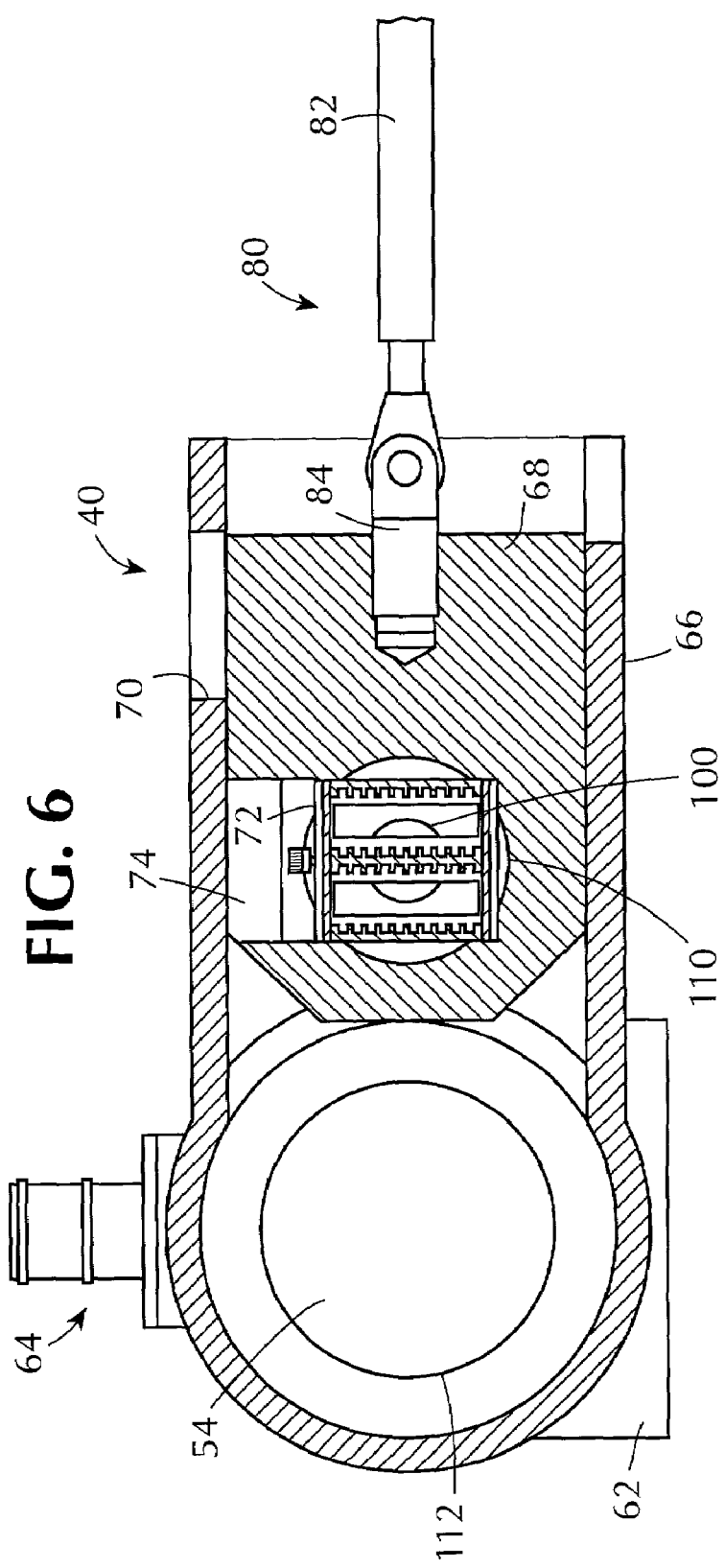
FIG. 6 is a cross-sectional front view similar to FIG. 5 but showing the shuttle and sample holder in the second (pre-treatment/post-treatment) position (in the antechamber)
Figure 7:
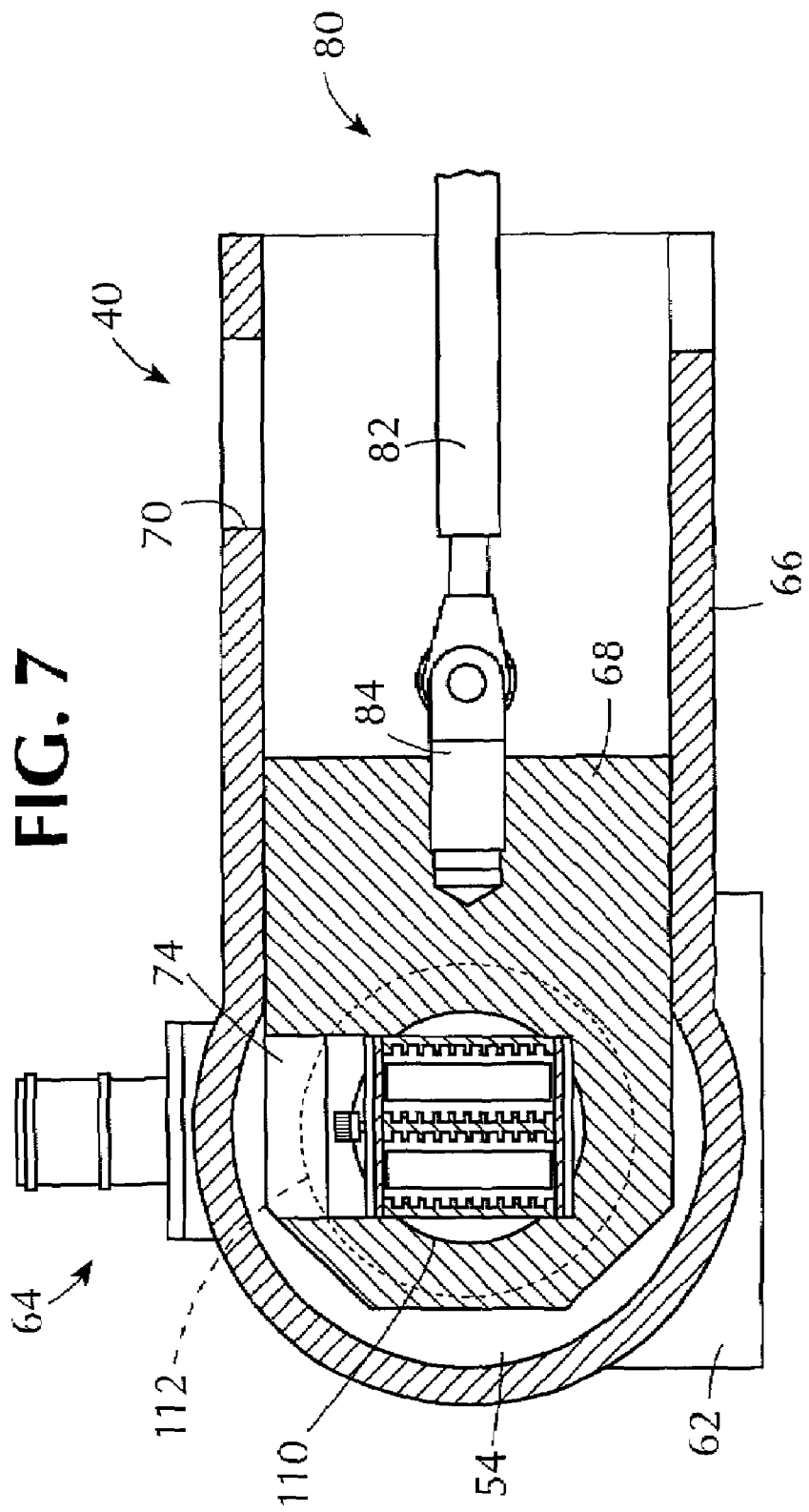
FIG. 7 is a cross-sectional front view similar to FIGS. 5 and 6 but showing the shuttle and sample holder in the third (exposure to antimicrobial) position (in the exposure chamber)

With reference now also to FIGS. 5, 6, and 7, shuttle 68 is moved between the three positions shown in those three figures by piston rod 86, which is moved in and out (to the left and to the right in FIGS. 1, 2, and 4) of cylinder 90. That piston assembly is pneumatically double actuated (to move the piston rod in either of the two directions). The movement of piston rod 86 is communicated to shuttle 68 through pushing/pulling mechanism 80 comprising adjustable connector 88, rod 82, and swivel connector 84, the end of which is connected to the outside end of shuttle 68.

Shuttle 68 has vertical bore 74, comprising vertical cylindrical bore 78 to which four vertical right-angled corners 76 have been added (best seen in FIGS. 1 and 4). The vertical concavity so formed is slightly larger in plan view from each corner 76 to its adjacent corners 76 than cartridge (specimen holder) 72, which is a rectangular parallelepiped, and thereby firmly retains cartridge 72 in place in a defined volume. Cartridge 72 measures 2.5 inches (6.4 centimeters) by 2.5 inches (6.4 centimeters) by 3.5 inches (8.9 centimeters), occupying a total volume of approximately 360 milliliters. When shuttle 68 is in the load position (as seen in FIGS. 1, 2, and 5), vertical bore 74 in shuttle 68 lies directly under access port 70 cut into pipe 66. Access port 70 has the same shape (in plan view) as vertical bore 74, thereby allowing cartridge 72 to be moved into and out of the defined volume (the volume at the bottom of vertical bore 74 containing cartridge 72). As best seen in FIGS. 5, 6, and 7, cartridge 72 has a number of grooves, thereby providing shelves for biological indicators (which may be roughly the shape of a microscope slide). To remove cartridge 72 from its closely fitting defined volume at the bottom of vertical bore 74, a knob at the top of cartridge 72 is grasped and pulled upward. Of course, cartridge 72, if used, may have any size or shape that allows the benefits of this invention to be achieved. Articles may be placed into the chamber without using any cartridge or any shuttle. The time required to move from the load position to the pre-treatment/post-treatment position is less than approximately 2 seconds.

In FIG. 6, shuttle 68 has been moved by pushing/pulling mechanism 80 from the first (load) position to the second (pre-treatment/post-treatment) position. Shuttle 68 has horizontal bore 110, whose longitudinal axis is perpendicular to the longitudinal axis of the shuttle. Bore 110 runs from one curved side of the shuttle, through the defined volume occupied by cartridge 72, to the other curved side of the shuttle. When shuttle 68 is in the load position (FIG. 5), the two ends of transverse horizontal bore 110 are blocked by the inner wall of pipe. When shuttle 68 is in the pre-treatment/post-treatment position (FIG. 6), the defined volume in shuttle 68 occupied by cartridge 72 is located in pre-treatment/post-treatment antechamber 102 (see FIG. 5), one end of bore 110 is aligned with opening 100 in the sidewall of pipe 66 (FIG. 6), and the other end of bore 110 is aligned with opening 104 in the sidewall of pipe 66. With reference also to FIG. 1, pre-treatment fluid (e.g., warm dry air) flows through inlet 94 (as shown by inlet flow arrow 96), through passageway 98, through opening 100, through the upstream portion of bore 110 in shuttle 68, through the defined volume occupied by cartridge 72 (thereby warming cartridge 72 and its contents, e.g., biological indicators), through the downstream portion of bore 110, and through outlet passageway 106 in outlet piping 108 (as shown by outlet flow arrow 120). In the embodiment shown in the figures, the warm dry air used as the pre-treatment fluid is flowed only when the shuttle is in the pre-treatment/post-treatment position (FIG. 6).

In FIG. 7, shuttle 68 has been moved by pushing/pulling mechanism 80 from the second (pre-treatment/post-treatment position) to the third (contact or exposure) position. Horizontal bore 110 of shuttle 72 is now open at both ends to exposure (main) chamber 54. The trailing portion of shuttle 72 (i.e., the portion closer to swivel connector 84) now blocks openings 100 and 104 in pipe 66. As noted above, shuttle 72 fits tightly within pipe 66. Thus, in the third position shuttle 72 fluidly isolates chamber 54 from antechamber 102, all the openings in that chamber, load position access port 70, and the open end of pipe 66. The time required to move from the pre-treatment/post-treatment position to the contact (exposure) position is less than approximately 2 seconds.

In chamber 54, antimicrobial gas is either already substantially continuously flowing at a substantially constant hydrogen peroxide concentration or that flow is suddenly commenced. In either case, the materials in the cartridge (e.g., sterilization indicators) are suddenly or rapidly brought into contact with the antimicrobial gas. In the embodiment shown in these figures, the gas is already flowing when the shuttle injects the cartridge into the flowstream.

With reference to FIG. 7, to reduce the amount of gas flowing around the leading edge of shuttle 68 (i.e., the left-most edge of the shuttle in FIG. 7), and thereby insure that substantially all of the antimicrobial gas flowing into chamber 54 flows through the predefined volume occupied by cartridge 72, the C-shaped open region around the leading edge may be blocked and/or the shape of the leading edge may be redesigned to reduce its size. Any other suitable method may be used. In the embodiment shown in the figures, a tube (not shown) was placed in exposure chamber 54 running from antimicrobial gas inlet 112 to where the upstream (inlet) end of bore 110 in shuttle 68 would be when the shuttle was in the exposure position (FIG. 7). The inlet end of the tube was approximately as big as opening 112 and the outlet end was approximately as big as the inlet end of bore 110 in the shuttle. The effect of this focusing tube was to help insure that substantially all of the antimicrobial gas flowing into chamber 54 flowed through the predefined volume occupied by cartridge 72. There did not need to be any similar sort of focusing device at the downstream (outlet) end of the horizontal bore in the shuttle.

After the desired contact time has expired, the contact of the materials is rapidly or suddenly halted, e.g., by rapidly halting the flow of the antimicrobial gas or by rapidly withdrawing the materials from the exposure chamber. In the embodiment of the figures, pushing/pulling mechanism 80 rapidly (in less than 2 seconds) moves the shuttle from the exposure position (FIG. 7) to the pre-treatment/post-treatment position of FIG. 6, where post-treatment is conducted. The flow of warm dry air through nozzle 94 etc. is recommenced, this time not to warm the cartridge and materials above the dew point of the hydrogen peroxide in the antimicrobial gas but to degas the cartridge and materials (i.e., remove any residual antimicrobial gas that may remain on them).

After the desired post-treatment time has expired, the shuttle is moved from the pre-treatment/post-treatment position (FIG. 6) to the load position (FIG. 5), where the cartridge containing the materials (e.g., biological indicators) is removed so that the sterilization indicators can be further processed (e.g., to determine how effective the contact with the antimicrobial gas was in killing the microorganism).

Figure 8:
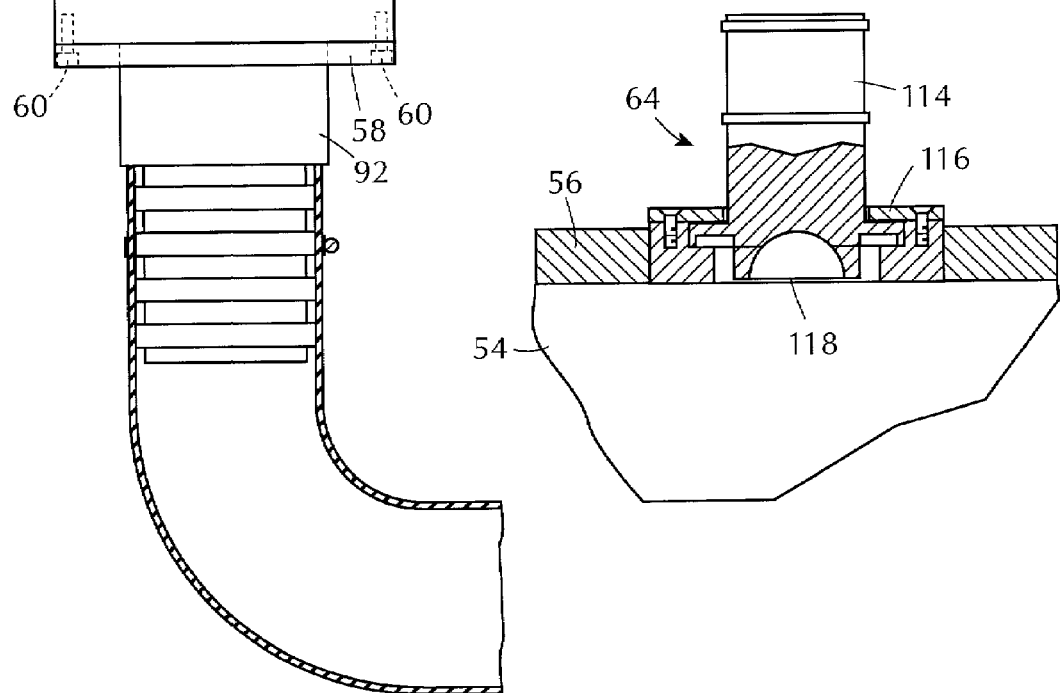
FIG. 8 is an elevation partial view of a device for detecting the presence of and determining the concentration of hydrogen peroxide inside the exposure chamber (Drager Sensor $H_2O_2$ HC, Model 6809070, manufactured by Dragerwerk AG and marketed by Draeger Safety, Inc.)

FIG. 8 shows Drager device assembly 64 comprises Drager device 114, which is held to pipe 56 by fastening assembly 116. The Drager device interrogates the contents of exposure chamber 54 through portal 118 and indicates concentration in milligrams of hydrogen peroxide per liter of the flowing antimicrobial gas.

The antimicrobial gas containing hydrogen peroxide is produced using novel apparatus and method that are the subject of a patent application being filed concurrently herewith entitled "Production of Hydrogen Peroxide Vapor-Air Mixtures," which application has previously been incorporated herein in its entirety for all purposes. That apparatus and method will be described in conjunction with FIGS. 9 to 12.

FIGS. 9 to 12 show details of the antimicrobial gas generator of FIGS. 2 and 3. The generator is used for producing a gas-phase flow of a carrier vapor or gas (e.g., air) combined with and containing the vapor resulting from vaporizing a liquid (e.g., an aqueous solution of hydrogen peroxide). The bulk liquid fed to the apparatus is converted by the apparatus into particulates and those particulates are entrained in the carrier. The carrier is in the gas phase and is a gas or is a liquid that has already been vaporized. The carrier entrains the particles of liquid of the vaporizable liquid and acts to vaporize those particles. Vaporization desirably occurs rapidly for a number of reasons, including that the surface area of the particulates is large compared to their volume (or mass) and that at the temperature of the carrier and particulates, the vapor pressure of the vaporizable liquid is sufficiently high. If the carrier is itself a vapor, the temperature should be high enough so that the carrier vapor does not condense.

The apparatus of FIGS. 9 to 12 desirably provides a product (i.e., effluent from the apparatus) that contains substantially no liquid, i.e., is substantially in the gas phase. In other words, in the apparatus of FIGS. 9 to 12, a sufficient proportion of the fine particles are vaporized in the apparatus so that the effluent from the apparatus contains substantially no liquid, i.e., is substantially in the gas phase. Thus, the effluent will contain no more than 10% w/w liquid-phase material, desirably no more than 8% w/w, more desirably no more than 6% w/w, most desirably no more than 4% w/w, preferably no more than 2% w/w, more preferably no more than 1% w/w, and most preferably no more than 0.5% w/w liquid-phase material.

The temperature of the gas-phase flow produced by the apparatus and method of FIGS. 9 to 12 can be (but need not be) relatively low. In other words, the temperature need not be anywhere as high as the boiling point of the vaporizable liquid. By "low-temperature," a "relatively low" temperature, and the like in connection with the gas-phase flow is meant a temperature below the boiling point, usually at least 20° C., desirably at least 30° C., more desirably at least 40° C., most desirably at least 50° C., preferably at least 60° C., more preferably at least 70° C., most preferably at least 80° C., and possibly even at least 90° C. lower than the boiling point of the vaporizable liquid.

The normal (atmospheric) boiling point of hydrogen peroxide is approximately 151° C. Thus, for hydrogen peroxide, the apparatus and method of FIGS. 9 to 12 when operated at atmospheric pressure can produce a gas-phase flow containing vaporized hydrogen peroxide at a temperature less than the normal boiling point and desirably much lower. At atmospheric pressure, the boiling point of pure water is 100° C. The apparatus and method of FIGS. 9 to 12 when operated at atmospheric pressure can produce a gas-phase flow containing vaporized water at a temperature less than the normal boiling point and desirably much lower. When using a 30% w/w aqueous solution of hydrogen peroxide as the vaporizable liquid (the normal boiling point of which is approximately 105° C.), the apparatus and method of FIGS. 9 to 12 when operated at approximately atmospheric pressure can produce a gas-phase flow of air as the carrier containing the completely vaporized aqueous hydrogen peroxide solution at temperatures that are as low as 0° C. to 80° C.

As will be understood by one skilled in the art, the heat needed to vaporize the vaporizable liquid (latent heat of vaporization) will be supplied by (transferred from) the carrier gas and will also be supplied by the vaporizable liquid itself. Thus, the carrier gas and the vaporizable liquid may enter the vaporization plenum at a temperature somewhat higher than the temperature of the final gas-phase product leaving the vaporization plenum. The vaporization of the vaporizable liquid will reduce the sensible temperature of the gas-phase mixture leaving the vaporization plenum if no other heat is added to the system. However, additional heat can be supplied to the system through, for example, the wall of the vaporization plenum. That additional heat may be the same as or more or less than the amount of heat required to vaporize the vaporizable liquid, thereby allowing further control of the temperature of the final gas-phase mixture.

The apparatus of FIGS. 9 to 12 allows such fine control that the vaporized vaporizable liquid in the total (effluent product) gas-phase flow can be present in any amount, namely, complete saturation or any level of unsaturation (i.e., from more than 99% of saturation to less than 1% of saturation). In this context, the term "unsaturated," "unsaturation," and the like refer to the vaporized vaporizable liquid not being present in the gas-phase product of the apparatus of FIGS. 9 to 12 in the amount that would constitute full saturation under the specified conditions.

The method and apparatus of FIGS. 9 to 12 are used to produce a gas-phase flow containing a substantially constant concentration of the vaporized vaporizable liquid (also referred to as the "second substance") over the time period of interest. By "substantially constant hydrogen peroxide concentration as a function of time," "substantially constant second substance concentration as a function of time," and the like is meant that the concentration of the hydrogen peroxide or other second substance (vaporizable liquid) in the gas-phase flow remains substantially constant over the time period of interest. In this context, "substantially constant" means that over the time period of interest, no concentration within that time period varies from the mean time-averaged concentration over that period by more than plus or minus 15%, desirably by no more than plus or minus 10%, more desirably by no more than plus or minus 8%, most desirably by no more than plus or minus 6%, preferably by no more than plus or minus 4%, more preferably by no more than plus or minus 2%, and most preferably by no more than plus or minus 1%. In other words, none of the instantaneously measured concentrations of the hydrogen peroxide or other second substance deviates from the average by more than plus or minus 15% of the average value, desirably by no more than plus or minus 10% of the average value, more desirably by no more than plus or minus 8%, etc.

The gas-phase flow (i.e., the entire flow out of the apparatus of FIGS. 9 to 12) is "substantially continuous," by which is meant that the flow satisfies at least one of the following criteria: (a) over the time period of interest, the minimum flow out of the apparatus is at least 50% (desirably at least 60%, more desirably at least 70%, most desirably at least 75%, preferably at least 80%, more preferably at least 85%, and most preferably at least 90%) of the maximum flow out of the apparatus, or (b) over the time period of interest, each of the minimum and maximum flows out of the apparatus differ from the time-average flow out of the apparatus by no more than 30% (desirably by no more than 25%, more desirably by no more than 20%, most desirably by no more than 15%, preferably by no more than 12.5%, more preferably by no more than 10%, and most preferably by no more than 7.5%) of the time-average flow out of the apparatus, or (c) over the time period of interest, the time-average flow for each successive minute-long period is at least 60% (desirably at least 70%, more desirably at least 75%, most desirably at least 80%, preferably at least 85%, more preferably at least 90%, and most preferably at least 95%) of the time-average flow out of the apparatus.

The fine particles of vaporizable liquid that are introduced into the flow of the carrier gas or vapor (i.e., the first substance) are desirably as small as possible so that the surface-to-volume (or mass) ratio is as large as is needed to allow the advantages of the apparatus of FIGS. 9 to 12 to be achieved. Particle sizes in the micron range will generally be used. Thus, the average particle size can range from 10 to 100 microns (desirably 10 to 50 microns), although smaller and larger particles may be used in certain cases. For example, if the flow of carrier gas or vapor is high compared to the flow of particles of vaporizable liquid, the temperatures are high enough, the vapor pressure of the vaporizable liquid is relatively high, the vaporization plenum is long enough, and the final concentration of vaporized vaporizable liquid in the gas-phase flow to be produced by the apparatus is not too close to saturation, the particles may be relatively larger than they would otherwise need to be. For 30% w/w aqueous hydrogen peroxide, an average particle size of 18 microns has been found to be satisfactory for the device described below. Desirably, the distribution of particle sizes is not too broad. In other words, preferably, 80% or more of the particles are within plus or minus 70% of the average particle size.

Breaking the vaporizable liquid into fine particles can be accomplished in any way that provides particles that are small enough and that flow inside the vaporization plenum in the desired direction. Devices such as atomizers or ultrasonic devices may be used. For a 30% w/w aqueous solution of hydrogen peroxide, a Sono-Tek brand ultrasonic device (Nozzle Model No. 12385, Generator Model No. 06-05112) has been found to be satisfactory as part of the apparatus of FIGS. 9 to 12 described below.

The vaporization plenum can have any size or shape that allow the advantages of the apparatus of FIGS. 9 to 12 to be achieved, although a cylindrical shape is preferred. The material of construction for the vaporization plenum and the rest of the apparatus can be anything that is sufficiently inert with respect to the substances that are present, e.g., flowing in the vaporization plenum. Thus, for a final gas-phase flow of air, water, and hydrogen peroxide (the hydrogen peroxide and most, if not all, of the water coming from the vaporizable liquid when it is an aqueous solution of hydrogen peroxide), the vaporization plenum can be made of aluminum (e.g., 6061 non-anodized), stainless steel (e.g., type 316 stainless steel), or any other suitable material.

An important feature is that in the vaporization plenum, the first substance (e.g., air) and the fine particles of the second substance (e.g., aqueous solution of hydrogen peroxide) are introduced in such a way that the particles are kept from touching the inner surface of the vaporization plenum. That is done because liquid particles that contact the inner surface of the vaporization plenum are less likely to be vaporized and/or are less likely to be vaporized completely. That results in the effluent gas-phase flow not having a substantially constant concentration of the vaporizable substance as a function of time. In other words, because it is important that the concentration of the vaporizable substance be substantially constant as a function of time, the particles of that substance introduced into the vaporization plenum must vaporize completely but if those particles contact the inner surface of the vaporization plenum, it reduces the chances of such complete vaporization.

If the vaporization plenum is cylindrical and the bulk flow is from one circular end (i.e., the entrance) of the cylinder towards the other end (i.e., the exit end), the particles of vaporizable liquid may be introduced at any point along the longitudinal center line of the vaporization plenum between the two ends (provided substantially complete vaporization of the vaporizable liquid occurs), with the bulk flow of the particles flowing towards the exit end of the vaporization plenum. Regardless of the shape of the vaporization plenum, the first substance (the carrier) may be introduced in any manner and in any orientation that places at least some (i.e., at least a sufficient amount) of the first substance between the inner surface of the vaporization plenum and substantially all of the fine particles to provide a curtain of the first substance between the inner surface of the vaporization plenum and substantially all of the fine particles. There may be more than one point of introduction into the vaporization plenum of each of the first and second substances, and those points may or may not be symmetrically arranged (e.g., may or may not be symmetrically arranged around the longitudinal centerline of the vaporization plenum).

Providing the curtain of carrier is important because the presence of that curtain greatly diminishes the number of collisions of the fine particles of the vaporizable substance with the inner surface of the vaporization plenum by keeping the particles away from the inner surface. Therefore, any method of introducing the first substance and fine particles of second substance into the vaporization plenum can be used as long as a curtain of the first (carrier) substance is provided to shield the inner surface of the vaporization plenum from substantially all of the fine particles. In this context, the term "substantially all of the fine particles" and like terms mean that no more than 10%, desirably no more than 8%, more desirably no more than 6%, most desirably no more than 4%, preferably no more than 2%, more preferably no more than 1%, and most preferably no more than 0.5% of the fine particles contact the inner surface of the vaporization plenum. Ideally no more than 0.1% of the fine particles contact the inner surface of the vaporization plenum.

The curtain need not be of uniform thickness. Thus, for example, with a cylindrical vaporization plenum, it is not necessary that the first substance (carrier), e.g., air, be introduced through an annular ring of constant width (which would tend to make the curtain of the carrier of uniform thickness. The carrier can have any flow pattern that provides the benefits of the apparatus of FIGS. 9 to 12. For example, the curtain may have a spiral or corkscrew flow pattern, which could be achieved by introducing the carrier into the vaporization plenum through passageways at an acute angle to the inner surface of the vaporization plenum.

The second substance (the vaporizable liquid) may be introduced into the vaporization plenum in any manner and in any orientation. The fine particles of the second substance (vaporizable liquid) need not be introduced at only one point into the vaporization plenum. For example, the carrier and particles of vaporizable liquid may each be introduced through a number of different openings into the vaporization plenum and those openings may be distributed or interspersed among each other. The only requirement is that the curtain of carrier (first substance) be created.

As will be understood by one skilled in the art, in addition to the temperature of the first and second substances and the size of the fine particles, another factor that helps determine whether a sufficient amount of the fine particles are vaporized so that the effluent from the apparatus contains substantially no liquid (i.e., is substantially in the gas phase) is the residence time of the fine particles in the apparatus. That in turn depends on the length of the device and the linear velocity of the particle flow.

The velocity of the fine particles when they are first injected into the vaporization plenum is desirably not greater than the velocity of the carrier. In any case, for several reasons, including the relative mass flows of the carrier and fine particles, the fine particles rapidly assume substantially the same velocity and direction as the carrier and therefore are carried towards the exit of the apparatus by the carrier (i.e., the first substance, which is a gas or is itself a vapor) at substantially the same linear velocity as the linear velocity of the first substance (carrier). Depending on the size, shape, and density of the fine particles, the density of the carrier, etc., the linear velocity of the carrier may vary from 0.1 centimeters/second to more than 50 centimeters/second but generally will be in the range of 0.1 to 25, desirably 0.1 to 10, and preferably from 0.1 to 5 centimeters/second.

Figure 11:
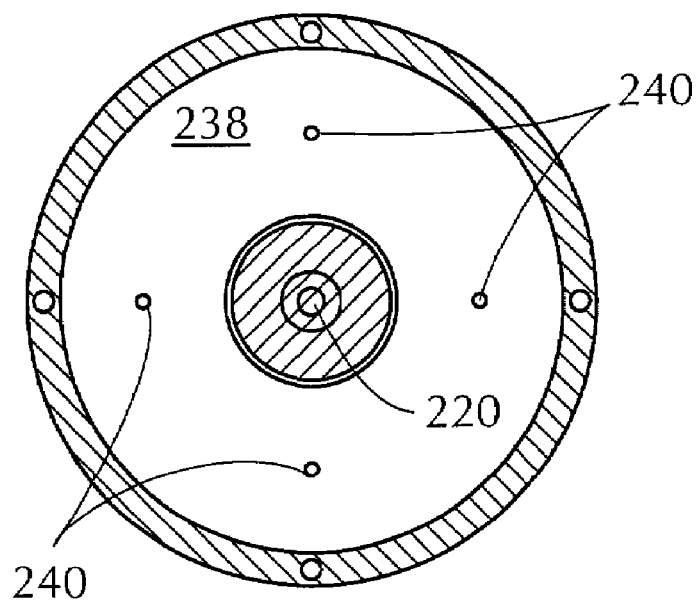
FIG. 11 is a view of the vaporization plenum of a device of FIG. 9 or FIG. 10 looking down in FIG. 9 or 10 at the vaporization plenum (with conduit 256 and nipple 252 removed) and showing a preferred air distributor and ultrasonic nozzle in the middle.

The direction of the bulk flow of a fluid (carrier, fine particles of vaporizable liquid, vaporized vaporizable liquid) in the apparatus is the major or principal direction of the overall flow and ignores the intermixing, lateral movement, etc. of the individual volumetric subdivisions (i.e., packets) of the fluid. For the entire apparatus, the direction of bulk flow is from the introduction of that fluid to the exit of the device; however, at any point along the fluid path inside the apparatus, the direction of bulk flow may be at any orientation with respect to the direction of the overall flow. That is because the fluid path inside the apparatus need not be straight from entrance to exit and can have any path, bent, crooked, winding, serpentine, spiral or corkscrew, or otherwise. However, as will be understood by one skilled in the art, a straight path, particularly in the vaporization plenum, is preferred.

The apparatus can be oriented so that the direction of bulk flow for the entire apparatus is in any direction and so that the direction of bulk flow of the fluid inside the vaporization plenum is in any direction; however, preferably the direction of bulk flow of all fluids inside the vaporization plenum has an upward vertical component and preferably is substantially upwardly vertical, as shown in FIGS. 2 and 3. By the term "substantially upwardly vertical," "up and substantially vertical," and the like is meant that the direction of bulk flow of the fluid inside the vaporization plenum is up and does not deviate from the vertical by more than 25°, desirably by no more than 20°, more desirably by no more than 15°, most desirably by no more than 10°, preferably by no more than 5°, more preferably by no more than 2°, and most preferably by no more than 1°. A substantially upwardly vertical flow of the fluid inside the vaporization plenum helps increase the chances that the fine particles of vaporizable liquid will be substantially all vaporized in the vaporization plenum. If the direction of bulk flow of the fluid inside the vaporization plenum is other than substantially upwardly vertical, it increases the chances that the fine particles of vaporizable liquid will contact the inner surface of the vaporization plenum and not be completely and rapidly vaporized.

For a droplet about 20 microns in diameter having a specific gravity of about 1.1 (i.e., a density of about 1.1 grams/cubic centimeter), with air as the carrier, operating around atmospheric pressure and at a temperature of about 50° C., and in a device in which the bulk flow of the fluid inside the vaporization plenum is vertical (i.e., directly against the force of gravity), the calculated minimum linear velocity of the air is approximately 2.7 centimeters per second (based on certain assumptions made concerning various factors, e.g., drag coefficient) so that the droplet is buoyed by the air flow and does not fall down. That velocity can be provided by adjusting the volumetric (or mass) flow of the air into the device and/or by choosing an appropriate vaporization plenum cross-sectional area. As will be understood by one skilled in the art, the linear flow of carrier needed to provide sufficient lift to a particle depends on a number of factors, including the particle size and shape, the density of the particle, and the density of the carrier. As will also be understood by one skilled in the art, if the theoretical minimum linear velocity of the air should be approximately 2.7 centimeters per second, the minimum linear velocity of air leaving the openings that feed the air into the vaporization plenum should be substantially higher (principally because the cross-sectional area of the openings is much smaller than the cross-sectional area of the vaporization plenum).

In FIG. 9, antimicrobial gas generator 42 comprises cylindrical vaporization plenum 212 having inner surface 214. Vaporization plenum is bounded at its ends by surface 238 of cylindrical end block 232 and exit 272. Cylindrical end block 232 is held in place by screws 246.

Screws 248 hold inner collar or ring 250 in place near exit 272. Inner ring 250 is threaded on its inner surface. Threaded portion 254 of nipple 252 screws into inner ring 250. Conduit 256 is press-fit onto nipple 252 and is also held in place by a circumferential compression band (not shown). Conduit 256 (analogous to duct 46 in FIGS. 1, 2, and 3) provides a passageway for the gas-phase effluent to leave the apparatus.

Warm dry air is introduced into vaporization plenum 212 through tube 226, which is connected to nozzle 228. The feed air flows through nozzle 228 into toroidal plenum 236, fills the toroidal plenum, and flows into vaporization plenum 212 through four openings 240 (only two of which are shown in FIG. 9; all four openings 240 are shown in FIG. 11). Air flow lines 242, whose direction of bulk flow is indicated by parallel arrows 244, illustrate the flow of air into vaporization plenum 212. As will be understood by one skilled in the art, the streamlines of air jetting out of openings 240 fan out.

Ultrasonic unit 218 is powered through an electric cord (not shown). Screw 234 holds plate 230 tightly against the outer surface of cylindrical end block 232, thereby holding ultrasonic unit 218 in place. Hydrogen peroxide solution (30% w/w aqueous solution) flows through inlet (feed) tube 217 into the ultrasonic unit, in which the flow of liquid is broken into fine particles approximately 18 microns in diameter.

The fine particles of the vaporizable liquid (the 30% w/w aqueous solution) are flowed into vaporization plenum 212 through nozzle 220. Flow lines 222 indicate the flow of fine particles out of nozzle 220, and arrow 224 signifies the direction of bulk flow of those particles. That direction of bulk flow lies on imaginary centerline 216 of vaporization plenum 212, which line intersects surface 238 at a point (not shown). (As will be understood by one skilled in the art, centerline 216 continues without limit above the vaporization plenum and also runs through the longitudinal center of nozzle 220, through the rest of ultrasonic unit 218, and continues without limit below the apparatus.) The direction of bulk flow of the fine particles (arrow 224) and the direction of bulk flow of the air (arrows 244) are parallel to each other, i.e., lie in the same direction, and both are vertical. The direction of bulk flow of the air (arrows 244) is also parallel to centerline 216 of vaporization plenum 212. Finally, centerline 216, the direction of bulk flow of the fine particles (arrow 224), and the direction of bulk flow of the air (arrows 244) are also each parallel to the inner surface of cylindrical vaporization plenum 212. When referring to these lines and/or surfaces, by "substantially parallel" is meant that the lines and/or surfaces do not deviate from being parallel by more than 40°, desirably by no more than 20°, more desirably by no more than 15°, most desirably by no more than 10°, preferably by no more than 5°, more preferably by no more than 2°, and most preferably by no more than 1°.

As shown in FIGS. 9 and 11, openings 240 are symmetrically arranged around centerline 216, which line passes through the central opening of nozzle 220 from which the fine particles of liquid flow into the air in the vaporization plenum. Thus, the flow of fine particles is introduced into the flow of air along a line about which openings 240 are symmetrically located.

In this device, all of the air flows into the vaporization plenum between inner surface 214 of the vaporization plenum and the point at which the fine particles are fed (i.e., the tip of nozzle 220), and that air creates a curtain of air between substantially all of the fine particles and the inner surface of the vaporization plenum.

A device in accordance with FIGS. 9 and 11 was built and tested. A cylindrical 6061 non-anodized aluminum pipe with a wall thickness of about 0.25 inches (about 6.4 millimeters) was used for the vaporization plenum. Stainless steel (e.g., type 316) could also have been used. Whatever the material of construction, it desirably is machinable as well as being sufficiently inert to the fluids to be processed in it. The inner diameter of the pipe was approximately 4.5 inches (approximately 114 millimeters) and the length of the vaporization plenum (from inner surface 238 of cylindrical end block 232) to the beginning of nipple 252 was approximately 7 inches (178 millimeters) long. Cylindrical end block 232 was approximately 1.45 inches thick (37 millimeters). Toroidal plenum 236 had an inner diameter of approximately 2.25 inches (57 millimeters), was approximately 0.5 inches (12.7 millimeters) high, and its upper surface lay approximately 0.2 inches (5 millimeters) below inner surface 238. The ultrasonic unit was a Sono-Tek brand device (Nozzle Model No. 12385, Generator Model No. 06-05112). An electrical heating tape was wrapped around the outside of vaporization plenum 212 and sufficient heat was supplied to keep the temperature of the vaporization plenum wall above 30° C. (ambient temperature was approximately 22° C.). Conduit 256 was left uninsulated to allow heat to leave the system so that the temperature of the gas-phase flow of air and vaporized hydrogen peroxide aqueous solution would fall.

Warm dry (−40° C. dew point) air at 50° C. was introduced through tube 226 at the rate of 30 liters/minute (500 cubic centimeters/second). Flow was controlled using a Norgren proportional pressure control valve, Model No. VP5002PK4111100, and a Norgren in-line flow control valve, Model No. T1000A2800. Temperature was controlled using a Hot Watt air process heater, Model No. AH37-A-MF, and a Watlow temperature controller, Model Series 965. Aqueous hydrogen peroxide solution (30% w/w) at a temperature of 22° C. was fed to the ultrasonic unit at a rate of 180 microliters/minute. Flow was controlled using a Digichrom syringe pump, Model No. 2Q. The particles produced by the ultrasonic unit were approximately 18 microns in diameter.

At first, each of the four opening 240 was approximately 0.5 inches (12.7 millimeters) in diameter; however, the concentration of hydrogen peroxide in the resulting effluent gas-phase mixture was not as high as the calculated theoretical concentration. When the device was opened for visual inspection to determine the cause of the discrepancy, it was discovered that some of the fine particles of hydrogen peroxide solution had not been vaporized and had instead contacted the inner surface of the vaporization plenum and pooled and collected. Because the pooling occurred on the side of the vaporization plenum distant from air feed nozzle 228, it was suspected that that the linear velocity of air through the one or two openings 240 distant from air feed nozzle 228 was not high enough (as compared to the linear velocity of air flowing out of the openings closer to air feed nozzle 228) to keep the fine particles flowing out of ultrasonic nozzle 220 from contacting the inner surface on that distant side of the vaporization plenum. When smaller openings 240 approximately one-sixteenth of an inch (1.6 millimeters) in diameter were used (to try to equalize the flows out of the four openings 240), the pooling problem substantially disappeared and the hydrogen peroxide in the gas-phase effluent was therefore closer to the calculated theoretical value of about 2.0 milligrams of hydrogen peroxide per liter.

With the air and hydrogen peroxide solution flow rates and temperatures noted above, the concentration of hydrogen peroxide in the gas-phase effluent from the apparatus when equipped with the one-sixteenth inch holes was 1.8 milligrams of hydrogen peroxide per liter (about 90% of the calculated theoretical value of about 2.0 milligrams/liter). The temperature of the effluent was 30° C., at which temperature the saturation limit for air is approximately 3 milligrams per liter. Therefore, the apparatus was producing a gas-phase effluent that was approximately 60% saturated with respect to the hydrogen peroxide (1.8 divided by 3).

As a result, it is believed that the flow of carrier through the openings providing the curtain of carrier between the fine particles of the vaporizable liquid and the inner wall of the vaporization plenum should be "substantially equal." In this context, the term "substantially equal" and the like mean that the flow through any one of those openings should not deviate from the average value of the flow through all of those openings by more than 35% of the average value, desirably by no more than 30%, more desirably by no more than 25%, most desirably by no more than 20%, preferably by no more than 15%, more preferably by no more than 10%, and most preferably by no more than 5%.

Figure 10:
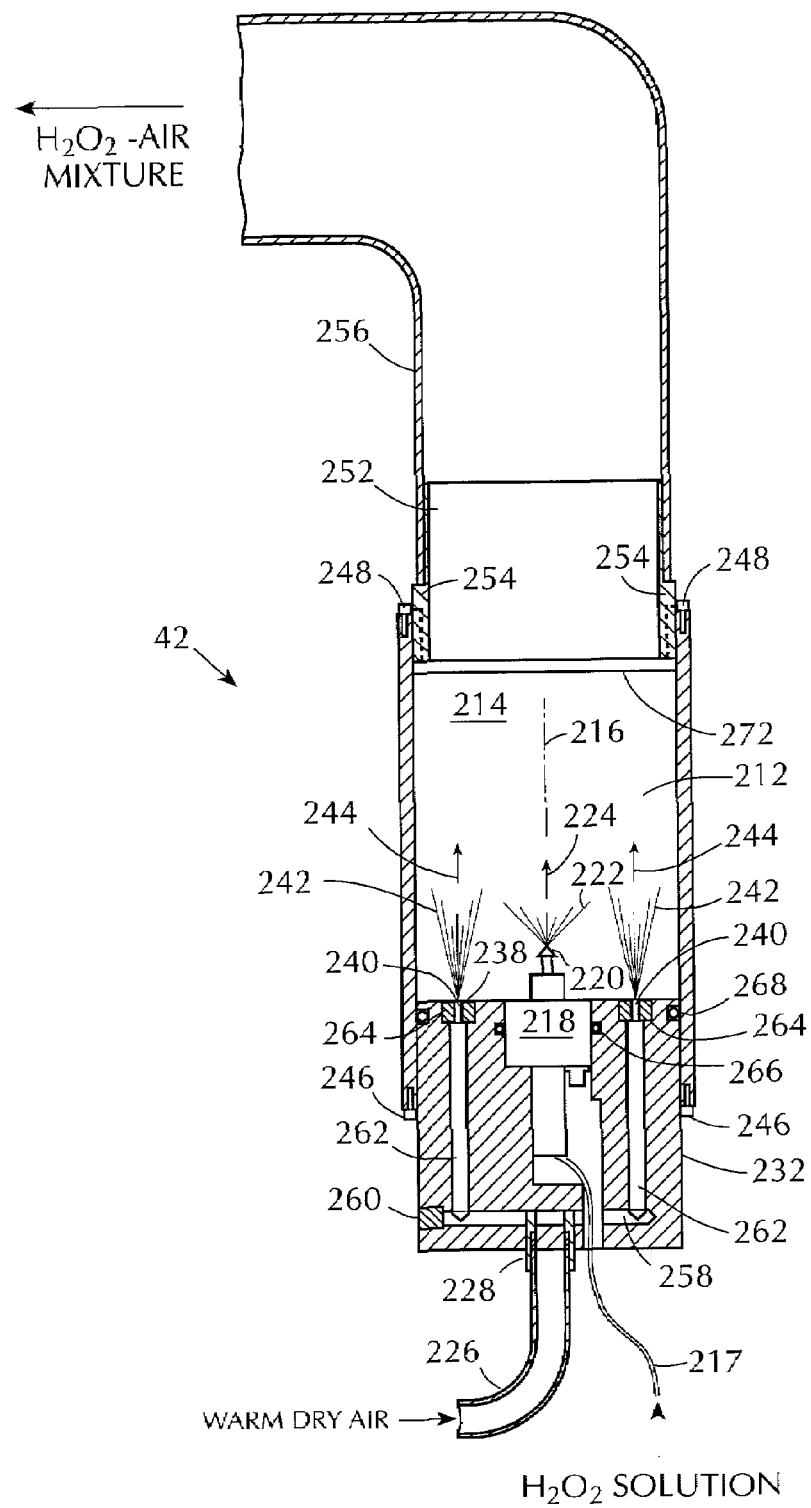
FIG. 10 is a side sectional view of a second apparatus that can be used as part of this invention for producing hydrogen peroxide vapor-air mixtures of substantially constant hydrogen peroxide concentration at substantially continuous flow rates.

Because of the inherent difficulty in producing equal air (carrier) flows through openings 240 when the point of introduction of the air into cylindrical end block 232 is closer to some of the openings than to others, a new design for the block was developed and is shown in FIG. 10. Air feed nozzle 228 is now centrally located and an internal X-shaped header comprising two elongate horizontal bores or passageways 258 at 90° to each other is used. The air is introduced through nozzle 228 at the center of the X, i.e., in the longitudinal (axial) center of cylindrical end block 232, where the two bores 258 intersect (in FIG. 10, only one of the bores 258 is shown). A plug 260 at the end of each bore 258 keeps the air from flowing out of cylindrical end block 232.

Four vertical bores or passageways 262 (only two of which are shown) are fluidly connected to the four legs of the X-shaped header formed by horizontal bores 258. Each bore 262 is capped by a plug 264 (only two of which are shown). A small diameter opening 240 of approximately one-sixteenth inch (1.6 millimeters) through each plug 264 allows air to flow into vaporization plenum 212. O-ring 266 between ultrasonic unit 218 and the larger cavity provided for it in cylindrical end block 232 and O-ring 268 between cylindrical end block 232 and the end of the pipe forming vaporization plenum 212 prevent fluid leakage, which was thought to be a problem with the device of FIG. 9.

The device of FIG. 10 is an improvement over the device of FIG. 9: it is believed to provide a more equal air flow through the four openings 240 than did the device of FIG. 9 even when the FIG. 9 device was equipped with the smaller openings. The device of FIG. 10 was operated with the same inlet flows and other conditions as the device of FIG. 9, and the resulting hydrogen peroxide concentration in the effluent from the device was 2 milligrams/liter, as compared to 1.8 milligrams/liter for the device of FIG. 9 with the smaller (one-sixteenth inch) holes. Thus, the vaporization efficiency of the device of FIG. 10 was almost 100% (as compared to the 90% vaporization efficiency of the FIG. 9 device with the smaller (one-sixteenth inch) holes. The effluent temperature was again 30° C., at which temperature the saturation limit for air is approximately 3 milligrams of hydrogen peroxide per liter. Thus, the gas-phase effluent was approximately 67% saturated with respect to hydrogen peroxide (2 divided by 3) but the vaporization efficiency was almost 100%. This demonstrates that the apparatus of FIGS. 9 to 12 can produce gas-phase effluents at virtually 100% vaporization efficiency but that are substantially less than saturated with respect to the vaporizable liquid.

The vaporization efficiency (i.e., the percentage of vaporized vaporizable liquid in the gas-phase effluents from those embodiments) can be (but does not necessarily have to be) a high percentage of the calculated theoretical value (calculated assuming that all of the vaporizable liquid fed is vaporized and is well-mixed with the carrier gas or vapor). As used herein, the terms "high vaporization efficiency," "highly efficient with respect to vaporization," and the like refer to the embodiments being able to produce effluents having such high percentages. Generally, the "high vaporization efficiency" of the antimicrobial gas generator will be at least 80%, desirably at least 85%, more desirably at least 90%, most desirably at least 95%, preferably at least 97%, more preferably at least 99%, most preferably at least 99.5%, and in some cases 100%.

Figure 12:
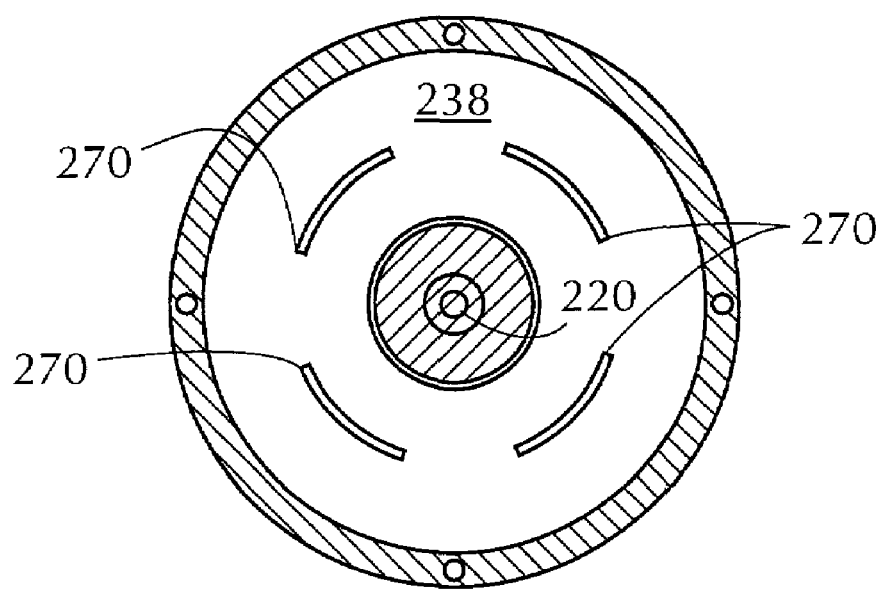
FIG. 12 is a view similar to that of FIG. 11 but with an alternative air distributor.

FIG. 12 shows a conceptual alternative design for the openings through which the carrier can be introduced (not yet built or tested). Arcuate slots 270 are symmetrically arranged around nozzle 220 of the ultrasonic unit and, as shown in FIGS. 9 and 10, the longitudinal centerline of nozzle 220 and arrow 224 lie along centerline 216 of vaporization plenum 212.

For a given carrier flow or range of carrier flows, one skilled in the art will know how to vary the shape and dimensions of the one or more slots (or other openings) to provide the necessary curtain of carrier to keep substantially all of the fine particles of the vaporizable liquid from the inner surface of the vaporization plenum.

The size of the openings through which the carrier is introduced will generally vary from less than a millimeter in equivalent diameter to 50 millimeters or more, depending on the flowrate of the carrier (by "equivalent diameter" is mean the diameter of a circle that would have the same area as the opening in question). For laboratory size units, the equivalent diameter will usually be from 0.1 millimeters to 25 millimeters, desirably from 0.1 to 20 millimeters, more desirably from 0.1 to 15 millimeters, preferably from 0.1 to 10 millimeters, more preferably from 0.1 to 5 millimeters, and most preferably from 0.1 to 2.5 millimeters. At least some of the carrier may be introduced into the vaporization plenum through members containing micropores, such as are present in sintered objects (e.g., sintered metal discs), provided the required curtain of carrier is formed.

The feed flowrates discussed above were 30 liters/minute of dry warm air and 180 microliters/minute of 30% w/w aqueous hydrogen peroxide solution. The range of feed flows can be from less than 1 liter per minute to hundreds or even more liters/minute of carrier and from just a few microliters per minute of vaporizable liquid to many liters per minute. Of course, the apparatus can be scaled up to provide even larger flows and/or be used at pressures other than atmospheric and/or be used at high temperatures; however, the apparatus of FIGS. 9 to 12 is particularly useful for producing, at high vaporization efficiency, low volume substantially continuous gas-phase flows at atmospheric pressure and at low temperature (e.g., an effluent temperature of 0–80° C. when hydrogen peroxide is the second substance derived from a 30% w/w aqueous solution of hydrogen peroxide) of substantially constant second substance (i.e., hydrogen peroxide) concentration even at second substance concentration levels below (even well below) saturation. The precisely controllable, continuously adjustable gas-phase flows produced by the antimicrobial gas generator are of particular use in, for example, testing and analytical devices, such as the device of FIGS. 1 to 7. Thus, the effluent flow rates will typically be from 0.1 liters per minute to 500 liters per minute, desirably from 0.5 to 250 liters/minute, more desirably from 0.5 to 200 liters/minute, preferably from 0.5 to 150 liters/minute, more preferably from 0.5 to 100 liters/minute, and most preferably from 0.5 to 50 liters/minute. Those flows are directed into exposure chamber 54 via duct 46.

FIG. 13 is a block system diagram. Compressed air is filtered, dried, and heated and flows into the evaporator (i.e., antimicrobial gas generator 42) and into antechamber 102 for pre-treatment and/or post-treatment. A pump transfers the aqueous hydrogen peroxide solution into the evaporator, and the antimicrobial gas containing the hydrogen peroxide flows into the main chamber (exposure chamber 54). The linear actuator moves the shuttle containing the cartridge from the antechamber into the main chamber. The Drager sensor (Drager device) outputs the hydrogen peroxide concentration of the gas inside the main chamber. The antimicrobial gas containing the hydrogen peroxide leaving the main chamber is also interrogated by the Analect FTIR spectrophotometer to determine hydrogen peroxide concentration. The Analect FTIR device need not be present if another suitable (e.g., sufficiently accurate) sensor is being used (e.g., the above-described Drager device that has been calibrated using the Analect FTIR). Finally, the antimicrobial gas is sent to a standard treatment unit to decompose the hydrogen peroxide.

Work was conducted to determine the efficacy, accuracy, reproducibility, etc. of the device of FIGS. 1–9 (but without temperature moderator 48, which, as noted above, has not been built). Thirty liters/minute of air and sufficient 30% w/w aqueous hydrogen peroxide were fed into antimicrobial gas generator 42 to produce a flow of antimicrobial gas containing 0.8 milligrams/liter of hydrogen peroxide (plus or minus 5% of the mean time-average value) at a flowrate of within plus or minus 3% of the 30 liters/minute. All of the flow was fed into main chamber 54. Five separate runs, each of 4 biological indicators containing *B. stearothermophilus* of population 1E6 (one million spores), were made in the following manner. For each run, the four biological indicators for that run were placed in cartridge 72 (FIG. 5), the cartridge was placed in the defined volume in shuttle 68, the shuttle was moved to the pre-treatment/post-treatment position (FIG. 6) and dry warm air (35° C.) was flowed through the cartridge for 5 minutes. The shuttle was then rapidly (less than approximately 2 seconds) moved from the pre-treatment/post-treatment position into exposure position (FIG. 7) and contacted for 5 minutes with the flowing antimicrobial gas containing the 0.8 milligrams/liter of hydrogen peroxide at 30° C. and approximately ambient atmospheric pressure. At the end of the 5 minutes, the shuttle was rapidly (less than approximately 2 seconds) moved from the exposure position to the pre-treatment/post-treatment position, where dry warm air at 35° C. was again flowed for 5 minutes through the cartridge to degas the biological indicators. The biological indicators were thereafter examined using standard methods to determine how many spores had survived.

Figures 14, 15:
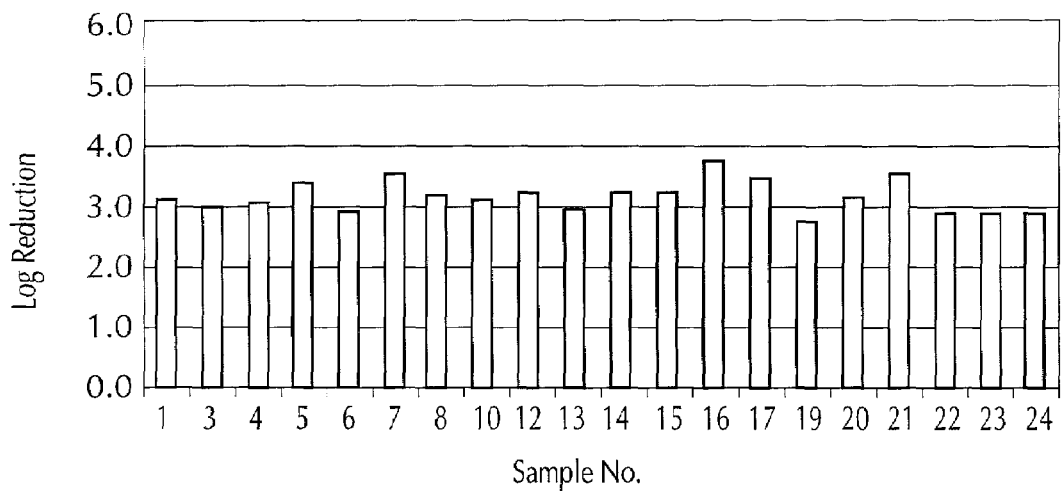
FIG. 14 is a table showing the results (number of spores remaining, etc.) of several test runs made using *Bacillus stearothermophilus* biological indicators (each initially containing one million spores) in a device of this invention.
FIG. 15 is a bar graph presenting the results of those runs to show the intra- and inter-run variation in the log reduction.

FIG. 14 shows the results for the 5 runs of 4 samples each. For quality control purposes, the four samples missing from FIG. 14 (nos. 2, 9, 11, and 18) were examined in the same way as the other twenty, but without going through the exposure procedure. Two survivor counts were made for each biological indicator, and those values are shown in the second and third columns of FIG. 14. The common logarithm of each survivor count was determined, and those values are reported in the fourth and fifth columns. The "log average" (average of the two logarithmic values) and range were determined (sixth and seventh columns). The eighth and last column shows the difference between the number 6.0000 (the common logarithm of 1,000,000, the original population size) and the log average survivor count. In other words, the last column shows the logarithm of the reduction in population size ("log reduction").

As can be seen in FIG. 15, the intra-run and inter-run log reductions were highly consistent. For example, for the first run, the values of samples 1, 3, 4, and 5 ranged from 3.0106 to 3.3753. The same closeness in values within a run is true for each of the other four runs. Furthermore, the values for each run are close to the values for each other run. This demonstrates the high accuracy and high reproducibility obtainable with the apparatus and method of this invention.

Further tests were made to determine if the Drager device, which costs only a small fraction of the cost of an FTIR spectrophotometer, could make accurate, reproducible determinations of the hydrogen peroxide concentration in the antimicrobial gas.

In conjunction with doing that, a hydrogen peroxide concentration curve for the FTIR spectrophotometer itself had to be determined, and that was accomplished using a method that is the subject of a patent application being filed concurrently herewith entitled "Spectrophotometric Determination Of Gas Phase Compositions," which application has previously been incorporated herein in its entirety for all purposes.

The method was used for establishing a monotonic functional relationship between the concentration of hydrogen peroxide and the integrated absorbance for a spectral region of interest.

It was known that pressure can effect the width of a peak in an absorbance spectrum for an analyte in a gas phase sample. It was also known that broadening of the absorption curve is accompanied by a reduction in the height of the peak; however, it was also thought that the area under the absorption curve, i.e., the integrated absorbance, would remain constant.

Accordingly, as will be further described below, it was surprising that for a constant amount of hydrogen peroxide (the analyte of interest) in the chamber in which the hydrogen peroxide was being measured by the FTIR instrument used, changing the amount of dry air in the chamber and therefore the total pressure would, below a certain pressure, have a significant effect on the absorbance of the hydrogen peroxide.

In addition to the pressure sensitivity of its spectral data, hydrogen peroxide decomposes in the vapor phase, thereby posing a challenge in trying to establish a monotonic functional relationship between integrated absorbance and concentration. Because hydrogen peroxide decomposes, its concentration decreases and the physical property indicative of the concentration (absorption) also decreases. Both of these problems (pressure sensitivity of the spectral data and decomposition) were overcome, and the monotonic functional relationship was established.

Samples of aqueous liquid solution of hydrogen peroxide (nominally 30% w/w) were used in the experiments. The hydrogen peroxide solution was obtained from VWR Scientific Products, located in West Chester, Pa. Just before its use, the hydrogen peroxide concentration was determined to be 30.2% w/w using a ceric sulfate titration. The density of the liquid solution was approximately 1.1 grams/cubic centimeter.

Samples were injected into a custom built device having a stainless steel chamber with a volume of 186 liters. Although the device was custom built, the design is not critical and any device can be used that allows the required data to be collected. A large chamber (such as one with a volume of 186 liters) has a number of benefits. For example, the ratio of its surface area to its volume is lower than that of a small chamber, and the decomposition of hydrogen peroxide is thought to be hastened by contact with surfaces. A larger chamber has a higher heat capacity as compared to a smaller chamber, thereby reducing variations in the temperature attributable to, for example, variations in ambient temperature and injection of the hydrogen peroxide and thereby facilitating temperature control. All the surfaces the analyte of interest contacts should be as inert as possible with respect to the analyte (e.g., should not promote its decomposition).

The chamber interior was coated with a thin layer of FOMBLIN brand perfluorinated grease obtained from Inland Vacuum Industries, Inc. (Churchville, N.Y.). The purpose of the grease was to render the inner surface of the chamber as inert as possible to reduce the rate of decomposition of the hydrogen peroxide.

The chamber walls were heated with hot air and electricity. Internal (chamber) pressure was measured in two ways, first, with an electronic transducer (pressure transducer type 122A, MKS Instruments, Inc., Andover, Mass.), which operates at pressures up to 100 torr, and second, with an analog gauge (Ametek U.S. Gauge, Sellersville, Pa.). Internal (chamber) temperature was monitored with an analog thermometer (Long Stem Thermometer, Model DF 10, Masterbuilt Mfg., Inc., Columbus, Ga.), whose probe extended into the interior of the chamber.

Aliquots of the hydrogen peroxide liquid solution were injected into the chamber with a syringe, the opening of whose needle was forced into the chamber through a resilient seal, much like the stopper-seal on a vial of medicine through which medical personnel can withdraw medicinal solutions with syringes for injection into patients. Vacuum was drawn on the chamber before injection of the hydrogen peroxide aliquots using a vacuum pump (Model RA 0025-E5Z6-1006, Busch, Inc., Virginia Beach, Va.). The pump could reduce the pressure in the chamber to about 2 torr if the pump were run for a sufficient time. The amount of solution injected for the various runs was typically not more than a few milliliters. For example, to obtain a concentration in the chamber of 1.135 milligrams of hydrogen peroxide per liter (1.135 mg/L), approximately 0.64 milliliters (0.7 grams) of the hydrogen peroxide liquid solution were injected. The temperature was, except for the temperature sensitivity runs, only a few degrees above ambient (typically approximately 35° C.). The warmth and low pressure in the chamber caused the small amount of liquid injected to flash into vapor rapidly upon injection. For non-quantitative studies, the aliquots were measured by volume in the syringe. For quantitative studies (i.e., studies in which the number of milligrams of hydrogen peroxide injected into the chamber had to be accurately known), the quantities of hydrogen peroxide solution to be injected were determined as the difference in weight of the syringe before and after the solution to be injected had been expelled from the syringe into the chamber.

Absorbance measurements were taken using the Fourier Transform Infrared (FTIR) spectrophotometer, Model No. TSO-20 marketed by Analect Instruments, Inc., located in Irvine, Calif. The optical path through the chamber was measured to be 18 inches (45.7 centimeters) and was sealed with salt windows, one sodium chloride and one potassium chloride. (The composition of the windows is not critical and any material can be used that allows the required data to be taken.) The bandpass was set at 4 $cm^{-1}$.

After drawing a vacuum on the chamber using the vacuum pump, sixty-four background scans were taken by the Analect FTIR instrument and averaged to obtain a background spectrum. The final value or measurement from the FTIR instrument is the integrated absorbance over the spectral range of interest. For hydrogen peroxide, the spectral region of 1180 $cm^{-1}$ to 1331 $cm^{-1}$ was used. In some cases, water was also determined, using two wavenumber regions, 1590 $cm^{-1}$ to 2030 $cm^{-1}$ and 3095 $cm^{-1}$ to 3912 $cm^{-1}$.

A known amount of hydrogen peroxide solution was injected into the chamber, and the hydrogen peroxide vaporized rapidly. Sufficient dry air from a compressed air cylinder at room temperature and 134.7 psia (928 kPa) was rapidly injected into the chamber to bring the pressure in the chamber to approximately atmospheric (raising the pressure to atmospheric required only about 30 seconds and was completed before commencement of the data scans described below). Using the concentration of hydrogen peroxide in the liquid solution, which was precisely known from the above-described analytical technique, the quantity of solution injected, which was carefully determined by weight difference (the weight of the syringe containing hydrogen peroxide solution minus the weight of the emptied syringe), and the volume of the chamber (186 liters), the initial vapor phase concentration of hydrogen peroxide was calculated in units of milligrams of hydrogen peroxide per liter.

A timer was started at the time of injection. Sixteen sample scans were taken for each data point. An interferogram resulted from each scan. The sixteen scans were combined and the required mathematical operations (Fourier transformation) were performed on the combination, thereby generating a single absorbance spectrum within the spectral region of interest for the analyte (1180 $cm^{-1}$ to 1331 $cm^{-1}$ for the hydrogen peroxide), and the integrated absorbance was calculated from that spectrum.

The sixteen FTIR instrument scans from which the integrated absorbance for each data point was calculated required a total of approximately 30 seconds to perform. For that first data point, the first scan of the set of sixteen scans started a little over 35 seconds after injection and the set of scans ended a little over 65 seconds after injection. The time for the single integrated absorbance value resulting from that set of scans was taken at the mid-point or slightly over 50 seconds.

The integrated absorbance for this set of scans (approximately 5.9) was plotted against the time mid-point of slightly over 50 seconds for the first data point. A second set of sixteen scans was started about 85 seconds after injection (about 20 seconds after the last scan of the first set) and ended about 115 seconds after injection. The integrated absorbance for the hydrogen peroxide for this second set of scans was calculated and that value was plotted against the time mid-point of 100 seconds. Four more successive points were determined in the same manner and were also plotted.

Using regression analysis and assuming that a straight line would fit the data over the time period shown, the respective concentration and absorbance data were associated by fitting them ($R^2$=0.9652) to the line y=−0.0031x+6.086 (y being the integrated absorbance and x being the elapsed time since the time of hydrogen peroxide injection). The y intercept value of 6.086 indicates that at time $t_o$ (the moment before decomposition began), the integrated absorbance was 6.086. In other words, if at the moment just before decomposition began the integrated absorption of the hydrogen peroxide for a concentration of 1.135 milligrams per liter could have been instantaneously determined, the value determined would have been 6.086.

In similar fashion, different known amounts of liquid hydrogen peroxide solution were injected, a set of FTIR scans was run for each selected time following injection, the integrated absorbance was determined for each such time, and the time $t_o$ integrated absorbance value was determined by fitting the data for each known initial vapor-phase hydrogen peroxide concentration and, in essence, extrapolating back to time zero (the moment just before decomposition began). These time $t_o$ absorbance values were used to obtain the monotonic functional relationship between the concentration of the vapor phase hydrogen peroxide analyte at the moment just before decomposition commenced and the integrated absorbance.

The data just discussed were obtained at a chamber pressure of approximately atmospheric pressure because dry air was added; however, when earlier runs were performed, dry air was not being added because there was no appreciation of the fact that the hydrogen peroxide spectral data were pressure sensitive. Without the addition of the dry air, the pressure in the chamber would be the pressure resulting from flashing of the small hydrogen peroxide liquid aliquots in the chamber plus the few torr of pressure resulting from the air in the chamber that the vacuum pump could not remove. After the pressure sensitivity was noticed, pressure sensitivity studies were conducted.

The integrated absorbance values as the total pressure was decreased below atmospheric pressure remained roughly constant at a value of about 5 until after the total pressure decreased below about 230 torr absolute. When the pressure was about 30 torr absolute, the integrated absorbance was only about 4. That means that although the initial concentration of hydrogen peroxide in units of mass of hydrogen peroxide per unit volume remained constant (because the same amount of hydrogen peroxide liquid solution is injected at the beginning of each run), and although one would therefore expect the integrated absorbance to remain constant regardless of the amount of dry air added to the chamber (the dry air does not react with the hydrogen peroxide or itself absorb in the spectral region used), it was found that the integrated absorbance fell by about 20% (from about 5 to about 4) at some point when the total pressure was below 230 torr. The effect of temperature on the spectral data was also investigated but was found to be insignificant.

Armed with the knowledge that the spectral data for hydrogen peroxide are pressure sensitive but not temperature sensitive within the pressure and temperature ranges of interest, spectral data were collected using the procedures described above on three separate days at a total chamber contents pressure of 20 kPa below atmospheric (an absolute pressure of about 610 torr) and a chamber contents temperature of about 48° C. The data from the three days were found to be consistent and were used together in one large data set to establish the monotonic functional relationship between concentration and absorbance for hydrogen peroxide.

The result of the data collection, Fourier transformation, etc. was a final data set consisting of initial (time $t_o$) hydrogen peroxide vapor phase concentrations and the respective time $t_o$ integrated absorbances (one integrated absorbance value for each concentration). Those data were then curve fit and the resulting line had the equation $y=4.7382x+0.4263$, where y is the integrated absorbance at initial time $t_o$ (the time immediately after injection of the known amount of hydrogen peroxide and immediately before hydrogen peroxide decomposition commences) and x is the calculated vapor phase hydrogen peroxide concentration at time $t_o$ in milligrams of hydrogen peroxide per liter. The fit was excellent (0.996 coefficient of correlation, 0.992 coefficient of determination, and 6.7% relative standard error of regression). The data points and the plot of the line are shown in the graph in FIG. 16.

Figure 16:
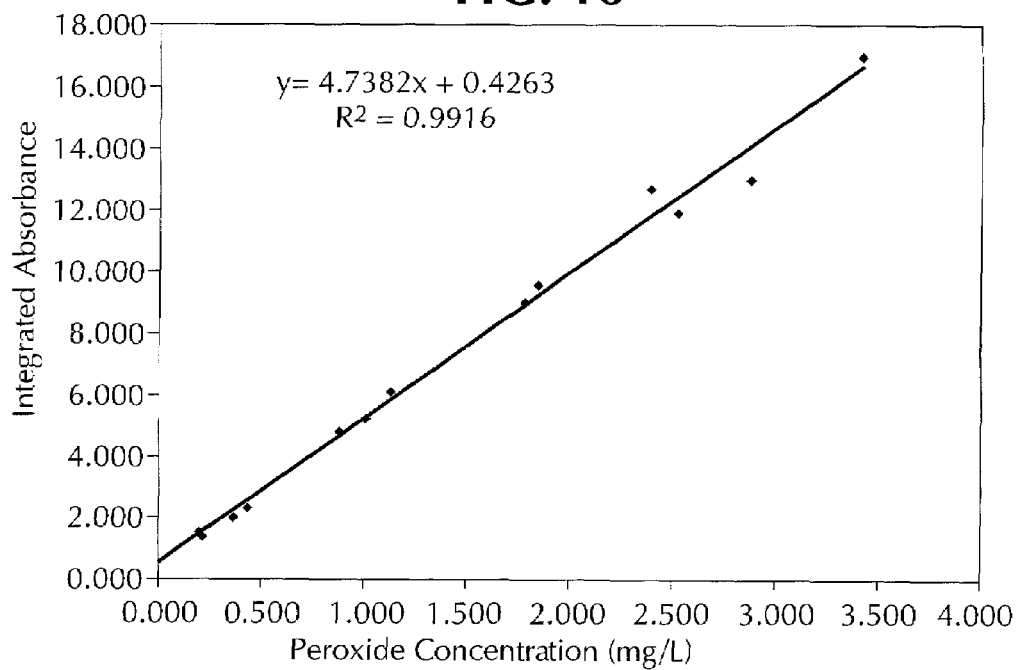
FIG. 16 is a graph of hydrogen peroxide concentration versus integrated absorbance obtained using a method employing the FTIR spectrophotometer.

The graph of FIG. 16 or the equation of the curve shown in that graph can be used to determine hydrogen peroxide concentration from integrated absorbance values determined for the same spectral region used to obtain the curve, with the same FTIR spectrophotometer path length, etc. A change in path length could easily be corrected for using the fact that absorption is directly proportional to path length and is directly proportional to concentration. The monotonic functional relationship once established can be used to calibrate the same instrument or other instruments (e.g., the Drager device), making appropriate corrections for any changes in path length etc.

Figure 13:
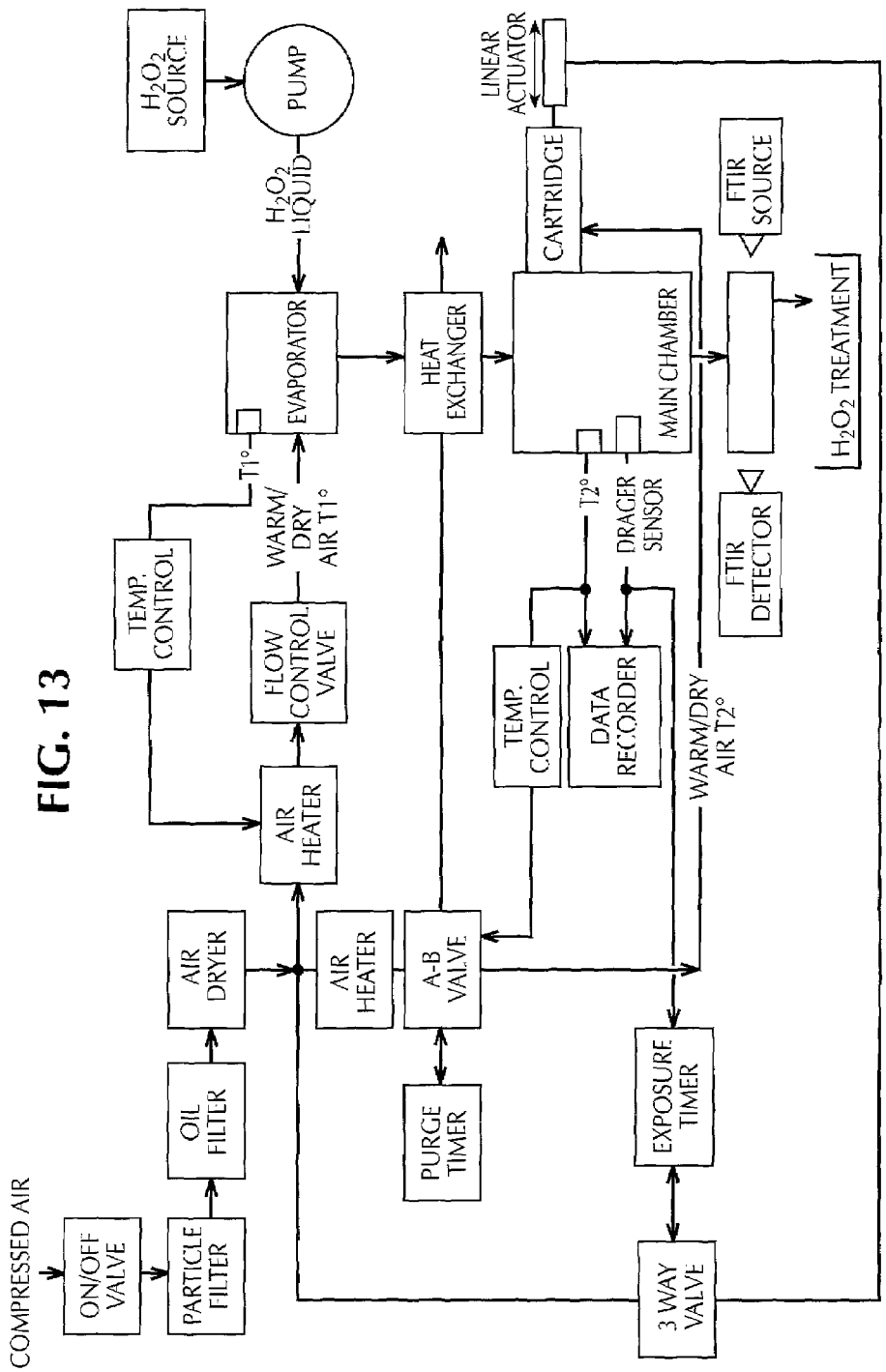
FIG. 13 is a block diagram of a system utilizing an embodiment of this invention.

The apparatus of FIGS. 1 to 9 (but without any specimens inside and with one modification described in the last sentence of this paragraph) was operated at 30 liters of air fed to antimicrobial gas generator 42 and different levels of 30% w/w aqueous hydrogen peroxide solution were fed by the pump to the generator. The Analect FTIR instrument was used to determine the hydrogen peroxide concentration in the effluent. As can be seen from FIG. 17, the two curves for the Analect FTIR spectrophotometer and the Drager device are essentially the same. Each of the two times the amount of hydrogen peroxide fed to antimicrobial gas generator was suddenly increased, both instruments registered the increase in the same time. For these runs, the Drager device was not in the position shown in FIGS. 8 and 13 but rather was positioned to read the concentration of hydrogen peroxide in the antimicrobial gas flowing into the FTIR tube (the tube between the FTIR source and the FTIR detector in FIG. 13) to allow simultaneous measurement of the same sample.

Figure 17:
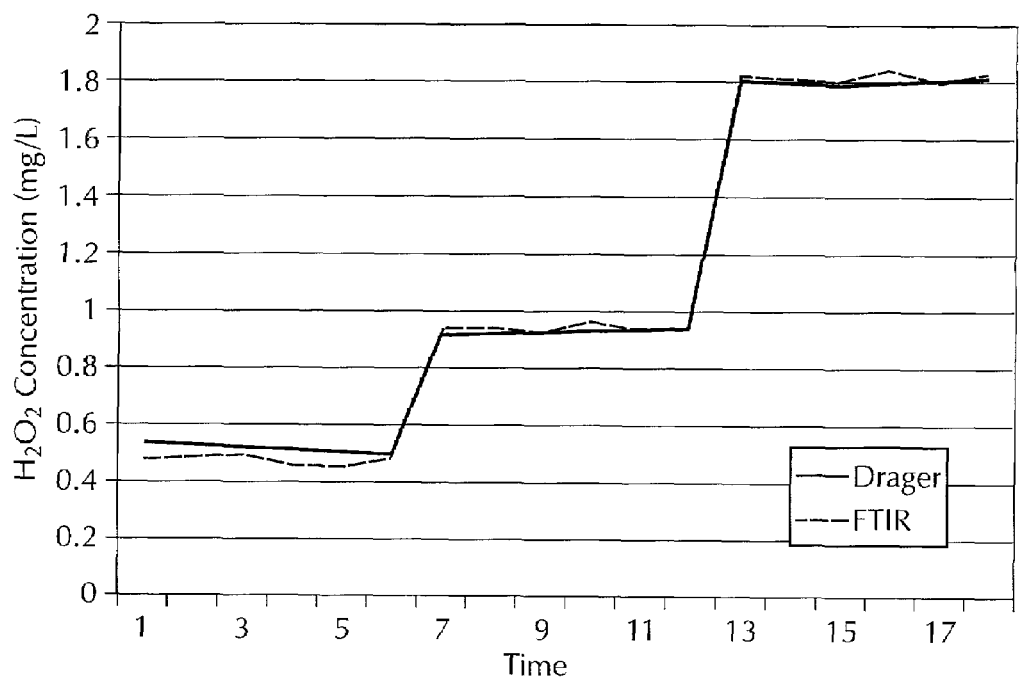
FIG. 17 is a graph comparing the hydrogen peroxide concentration determined with the Drager hydrogen peroxide detector to the concentration determined at the same time by a Fourier Transform Infrared (FTIR) spectrophotometer (Model No. TSO-20 marketed by Analect Instruments, Inc.) as the hydrogen peroxide was raised from one concentration level to the next.

A further set of runs were made using the same set-up as was used to generate the data for FIG. 17. Three sets each of six replicate hydrogen peroxide concentrations in the antimicrobial gas were run and the Drager hydrogen peroxide concentration values were plotted against the FTIR spectrophotometer integrated absorbance values (spectrum area) in FIG. 18. As shown in that figure, for each of the three concentration levels, there is little scatter in the data for either device. Furthermore, the equation of the line shows that the line had excellent fit ($R^2=0.9989$) and passes almost exactly through the origin (which it should).

Figure 18:
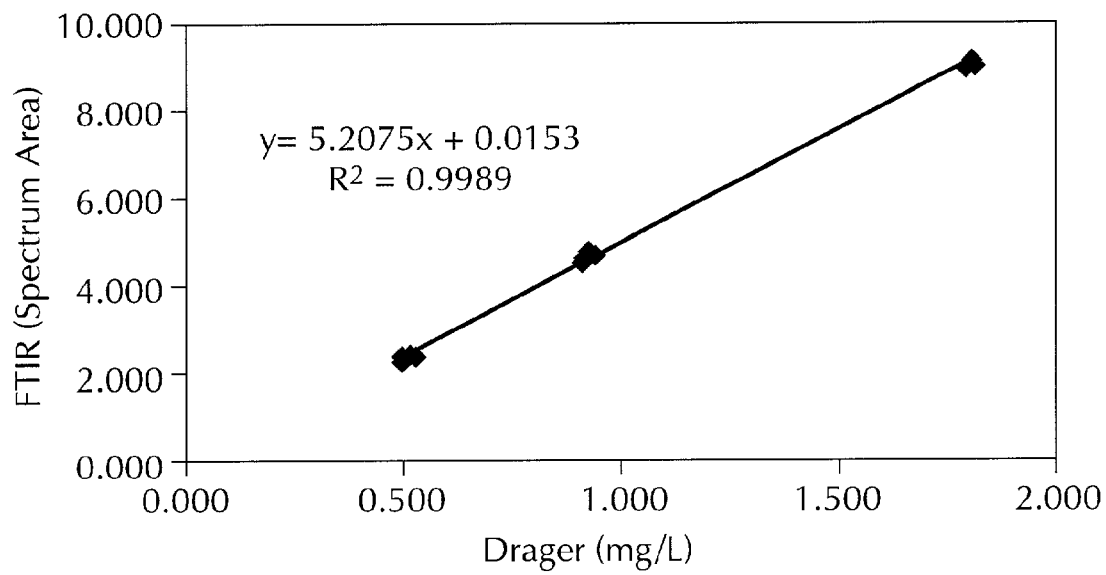
FIG. 18 is a graph showing, for three different hydrogen peroxide concentrations (six replicate runs for each concentration), the integrated absorbance (spectrum area) determined with the FTIR spectrophotometer and the concentration determined at the same time by the Drager detector.
Figure 19:
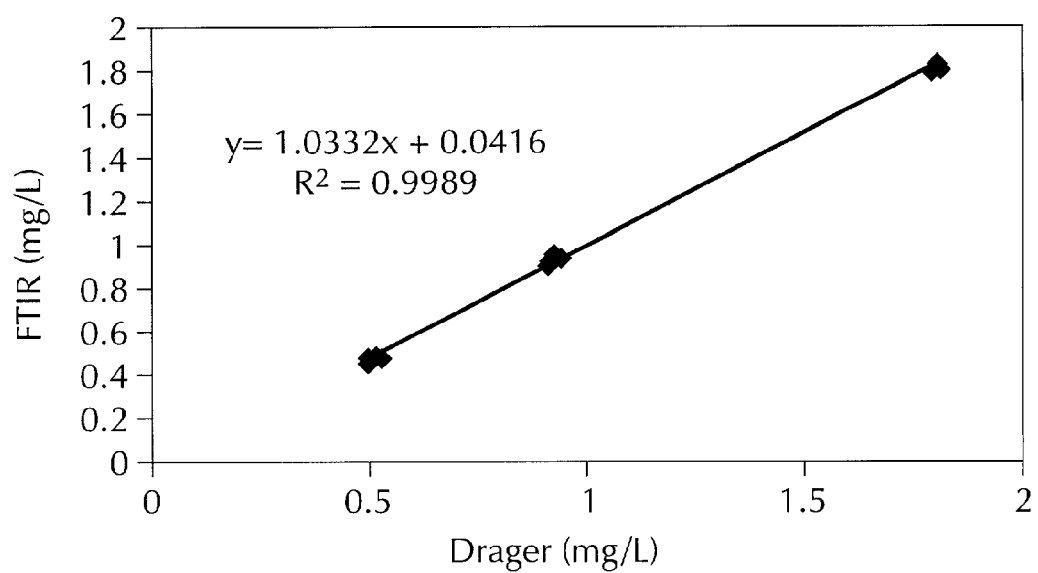
FIG. 19 is a graph comparing, for the same data as in FIG. 18, the concentration ultimately determined from the FTIR spectrophotometer (using the data of FIG. 18 and the absorbance-concentration relationship of FIG. 16) and the concentration determined by the Drager device and showing the high level of correlation between the concentrations determined by the two devices.

The FTIR data used for FIG. 18 were converted to concentration values using the data of FIG. 16. The result was FIG. 19, which shows the hydrogen peroxide concentration determined by the Drager device and the concentration for the same material determined at the same time by the FTIR spectrophotometer. Again, the fit of the data to the line is excellent and the line comes close to passing through the origin. This shows that once a Drager device is calibrated against the more exacting FTIR standard, the substantially less expensive Drager device can be used in the apparatus of this invention to make the necessary determination of hydrogen peroxide concentrations in the flowing antimicrobial gas. More generally, once any suitable but less expensive sensing device is calibrated against the more exacting FTIR standard, the less expensive device can be used in the apparatus of this invention to make the necessary determination of hydrogen peroxide concentrations in the flowing antimicrobial gas.

In summary, this invention is believed to provide the first hydrogen peroxide BIER/testing devices that produce accurate and reproducible results and that are flexible, rapidly provide uniform contact conditions, are precisely controllable, etc.

Variations and modifications will be apparent to those skilled in the art and the following claims are intended to cover all variations and modifications falling within the true spirit and scope of the invention. For example, the apparatus may be of any size or shape, may be made out of any suitable material, may be operated at almost any hydrogen peroxide concentration, temperature, pressure, etc. It may be used for any or all or the purposes set forth herein and it may be modified as necessary with regard to size, shape, material of construction, operating temperature, pressure, hydrogen peroxide concentration, etc. to achieve the benefits of this invention.

We claim:
1. An apparatus for testing one or more sterilization indicators by contacting them under controlled sterilization conditions with a flowing antimicrobial gas comprising hydrogen peroxide vapor, the apparatus comprising:
  (a) antimicrobial gas generating means for providing the flowing antimicrobial gas comprising hydrogen peroxide vapor, the antimicrobial gas generating means comprising:
    (1) a vaporization plenum having an inner surface;
    (2) means for breaking a vaporizable liquid comprising hydrogen peroxide into fine particles and for flowing the fine particles in the vaporization plenum, the bulk flow of the fine particles flowing in the vaporization plenum being in a first direction;
    (3) means for flowing a gas or vapor comprising a first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and
    (4) means for causing substantially all of the fine particles to vaporize in the flow of the first substance to produce a substantially continuous flow of a gas-phase mixture of the first substance and vaporized hydrogen peroxide of substantially constant hydrogen peroxide concentration as a function of time, the antimicrobial gas comprising the gas-phase mixture;
  (b) a chamber in which the one or more sterilization indicators can be contacted with the flowing antimicrobial gas;

(c) means for rapidly placing the one or more sterilization indicators in the chamber while the flow of the antimicrobial gas in the chamber is substantially continuous and the concentration of hydrogen peroxide in the antimicrobial gas is substantially constant as a function of time;

(d) means for continuing to flow the antimicrobial gas in the chamber to contact the one or more sterilization indicators from substantially the moment they are placed in the chamber, the contact being under substantially uniform conditions for the desired contact time, the flow of the antimicrobial gas during the contact being substantially continuous and the concentration of hydrogen peroxide in the antimicrobial gas during the contact being substantially constant as a function of time; and (e) means for rapidly removing the one or more sterilization indicators from the chamber after the desired contact time of the one or more sterilization indicators with the antimicrobial gas has elapsed.

2. The apparatus of claim 1 further comprising means for pre-treating the one or more sterilization indicators before their contact with the antimicrobial gas has commenced.

3. The apparatus of claim 1 further comprising means for post-treating the one or more sterilization indicators after they have been removed from the chamber.

4. The apparatus of claim 1 further comprising means for pre-treating the one or more sterilization indicators before their contact with the flowing antimicrobial gas has commenced and means for post-treating them after their contact with the flowing antimicrobial gas has halted.

5. The apparatus of claim 4 wherein the means for pre-treating and the means for post-treating comprise at least some of the same members.

6. The apparatus of claim 5 further comprising an antechamber wherein the means for pre-treating and the means for post-treating each comprise the antechamber.

7. The apparatus of claim 6 further comprising a movable member and means for moving the movable member from the chamber to the antechamber and from the antechamber to the chamber.

8. The apparatus of claim 7 wherein the means for rapidly placing the one or more sterilization indicators in the chamber and the means for rapidly removing the one or more sterilization indicators from the chamber after the desired contact time has elapsed are the same and each comprises the movable member.

9. The apparatus of claim 1 further comprising means to maintain the one or more sterilization indicators in a predefined volume in the chamber.

10. The apparatus of claim 9 further comprising means to flow substantially all of the antimicrobial gas flowing into the chamber through the predefined volume.

11. The apparatus of claim 1 further comprising means for monitoring the hydrogen peroxide concentration of the antimicrobial gas.

12. The apparatus of claim 1 further comprising means for maintaining the contact of the antimicrobial gas with the sterilization indicators at a desired temperature.

13. The apparatus of claim 1 wherein the antimicrobial gas generating means is oriented so that the first direction is up and substantially vertical.

14. A method for testing one or more sterilization indicators by contacting them under controlled sterilization conditions with a flowing antimicrobial gas comprising hydrogen peroxide vapor, the method comprising:

(a) rapidly placing the one or more sterilization indicators in the chamber of the apparatus of claim 1 or 4 while the flow of the antimicrobial gas in the chamber is substantially continuous and the concentration of hydrogen peroxide in the antimicrobial gas is substantially constant as a function of time;

(b) continuing to flow the antimicrobial gas in the chamber to contact the one or more sterilization indicators from substantially the moment they are placed in the chamber, the contact being under substantially uniform conditions for the desired contact time, the flow of the antimicrobial gas during the contact being substantially continuous and the concentration of hydrogen peroxide in the antimicrobial gas during the contact being substantially constant as a function of time; and (c) rapidly removing the one or more sterilization indicators from the chamber after the desired contact time of the one or more sterilization indicators with the antimicrobial gas has elapsed.

15. The method of claim 14 wherein the hydrogen peroxide concentration in the antimicrobial gas during the desired contact time does not vary from the mean time-averaged hydrogen peroxide concentration during that time by more than plus or minus 10%.

16. The method of claim 14 wherein the hydrogen peroxide concentration in the antimicrobial gas during the desired contact time does not vary from the mean time-averaged hydrogen peroxide concentration during that time by more than plus or minus 8%.

17. The method of claim 14 wherein the hydrogen peroxide concentration in the antimicrobial gas during the desired contact time does not vary from the mean time-averaged hydrogen peroxide concentration during that time by more than plus or minus 6%.

18. An apparatus for testing one or more sterilization indicators by contacting them under controlled sterilization conditions with a flowing antimicrobial gas comprising hydrogen peroxide vapor, the apparatus comprising:

(a) antimicrobial aas generating means for providing the flowing antimicrobial gas comprising hydrogen peroxide vapor, the antimicrobial gas generating means comprising:

(1) a vaporization plenum having an inner surface;

(2) means for breaking a vaporizable liquid comprising hydrogen peroxide into fine particles and for flowing the fine particles in the vaporization plenum, the bulk flow of the fine particles flowing in the vaporization plenum being in a first direction;

(3) means for flowing a gas or vapor comprising a first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and (4) means for causing substantially all of the fine particles to vaporize in the flow of the first substance to produce a substantially continuous flow of a gas-phase mixture of the first substance and vaporized hydrogen peroxide of substantially constant hydrogen peroxide concentration as a function of time, the antimicrobial aas comprising the gas-phase mixture;

(b) a chamber in which the one or more sterilization indicators can be contacted with the flowing antimicrobial gas;

(c) means for suddenly commencing the contact of the flowing antimicrobial gas with the one or more sterilization indicators in the chamber and means for continuing the contact of the flowing antimicrobial gas with the one or more sterilization indicators in the chamber under substantially uniform conditions for the desired contact time, the flow of the antimicrobial gas in the chamber during the contact being substantially continuous and the concentration of the hydrogen peroxide in the antimicrobial gas during the contact being substantially constant as a function of time; and (d) means for suddenly halting the contact of the antimicrobial gas with the sterilization indicators after the desired contact time has elapsed.

19. The apparatus of claim 18 further comprising means for pre-treating the one or more sterilization indicators before their contact with the flowing antimicrobial gas has commenced.

20. The apparatus of claim 18 further comprising means for post-treating the one or more sterilization indicators after their contact with the flowing antimicrobial gas has halted.

21. The apparatus of claim 18 further comprising means for pre-treating the one or more sterilization indicators before their contact with the flowing antimicrobial gas has commenced and means for post-treating them after their contact with the flowing antimicrobial gas has halted.

22. The apparatus of claim 21 wherein the means for pre-treating and the means for post-treating comprise at least some of the same members.

23. The apparatus of claim 22 further comprising an antechamber wherein the means for pre-treating and the means for post-treating each comprise the antechamber.

24. The apparatus of claim 18 further comprising means for monitoring the hydrogen peroxide concentratiQn of the antimicrobial gas.

25. The apparatus of claim 18 wherein the means for suddenly commencing and then continuing the contact of the flowing antimicrobial gas with the sterilization indicators comprises means for rapidly placing and maintaining the one or more sterilization indicators in the chamber while the flow of the antimicrobial gas in the chamber is substantially continuous and the concentration of the hydrogen peroxide in the antimicrobial gas is substantially constant as a function of time.

26. The apparatus of claim 18 wherein the means for suddenly halting the contact of the flowing antimicrobial gas with the sterilization indicators after the desired contact time has elapsed comprises means for rapidly removing the one or more sterilization indicators from the chamber after the desired contact time has elapsed.

27. The apparatus of claim 18 further comprising means to maintain the one or more sterilization indicators in a predefined volume in the chamber.

28. The apparatus of claim 27 further comprising means to flow substantially all of the antimicrobial gas flowing into the chamber through the predefined volume.

29. The apparatus of claim 18 wherein the antimicrobial gas generating means is oriented so that the first direction is up and substantially vertical.

30. A method for testing one or more sterilization indicators by contacting them under controlled sterilization conditions with a flowing antimicrobial gas comprising hydrogen peroxide vapor, the method comprising:

(a) placing them in the chamber of the apparatus of claim 18 or 21;

(b) suddenly commencing the contact of the flowing antimicrobial gas with the one or more sterilization indicators in the chamber and continuing the contact of the flowing antimicrobial gas with the one or more sterilization indicators in the chamber under substantially uniform conditions for the desired contact time, the flow of the antimicrobial gas in the chamber during the contact being substantially continuous and the concentration of the hydrogen peroxide in the antimicrobial gas during the contact being substantially constant as a function of time; and (c) suddenly halting the contact of the antimicrobial gas with the sterilization indicators after the desired contact time has elapsed.

31. The method of claim 30 wherein the hydrogen peroxide concentration in the antimicrobial gas during the desired contact time does not vary from the mean time-averaged hydrogen peroxide concentration during that time by more than plus or minus 10%.

32. The method of claim 30 wherein the hydrogen peroxide concentration in the antimicrobial gas during the desired contact time does not vary from the mean time-averaged hydrogen peroxide concentration during that time by more than plus or minus 8%.

33. The method of claim 30 wherein the hydrogen peroxide concentration in the antimicrobial gas during the desired contact time does not vary from the mean time-averaged hydrogen peroxide concentration during that time by more than plus or minus 6%.

34. An apparatus for testing sterilization processes that use a flowing antimicrobial gas comprising hydrogen peroxide vapor under controlled sterilization conditions, or for testing materials for such processes under controlled sterilization conditions, or for testing both such processes and such materials under controlled sterilization conditions, the materials comprising one or more articles, the apparatus comprising:

(a) antimicrobial gas generating means for providing the flowing antimicrobial gas comprising hydrogen peroxide vapor, the antimicrobial gas generating means comprising:

(1) a vaporization plenum having an inner surface:

(2) means for breaking a vaporizable liquid comprising hydrogen peroxide into fine particles and for flowing the fine particles in the vaporization plenum, the bulk flow of the fine particles flowing in the vaporization plenum being in a first direction;

(3) means for flowing a gas or vapor comprising a first substance in the vaporization plenum and for flowing at least some of the first substance between the inner surface of the vaporization plenum and substantially all of the fine particles to create a curtain of first substance between the inner surface of the vaporization plenum and substantially all of the fine particles, the bulk flow of the first substance in the vaporization plenum flowing in substantially the same direction as the first direction; and (4) means for causing substantially all of the fine particles to vaporize in the flow of the first substance to produce a substantially continuous flow of a gas-phase mixture of the first substance and vaporized hvdroaen peroxide of substantially constant hvdroaen peroxide concentration as a function of time, the antimicrobial gas comprising the gas-phase mixture;

(b) a chamber in which the antimicrobial gas is flowed to provide contact of any one or more of the articles with the antimicrobial gas when articles are in the chamber;

(c) means for flowing the antimicrobial gas in the chamber to contact any such one or more articles under substantially uniform conditions for the desired time, the flow of the antimicrobial gas in the chamber during the desired time being substantially continuous and the concentration of the hydrogen peroxide in the antimicrobial gas during the desired time being substantially constant as a function of time; and (d) means for halting the flow of the flowing antimicrobial gas after the desired time has elapsed.

35. The apparatus of claim 34 wherein means (c) comprises means for suddenly commencing and then continuing the flow of the antimicrobial gas in the chamber.

36. The apparatus of claim 35 wherein the means for suddenly commencing and then continuing the contact of the flowing antimicrobial gas with any one or more articles comprises means for rapidly placing and maintaining the one or more articles in the chamber while the flow of the antimicrobial gas in the chamber is substantially continuous and the concentration of the hydrogen peroxide in the antimicrobial gas is substantially constant as a function of time.

37. The apparatus of claim 34 wherein means (d) comprises means for suddenly halting the flow of the antimicrobial gas.

38. The apparatus of claim 37 wherein the means for suddenly halting the contact of the flowing antimicrobial gas with any one or more articles after the desired contact time has elapsed comprises means for rapidly removing the one or more articles from the chamber after the desired contact time has elapsed.

39. The apparatus of claim 34 wherein means (c) comprises means for suddenly commencing and then continuing the flow of the antimicrobial gas in the chamber and means (d) comprises means for suddenly halting the flow of the antimicrobial gas.

40. The apparatus of claim 34 further comprising means for pre-treating any one or more articles placed in the chamber before their contact with the flowing antimicrobial gas has commenced.

41. The apparatus of claim 34 further comprising means for post-treating any one or more articles placed in the chamber after their contact with the flowing antimicrobial gas has halted.

42. The apparatus of claim 34 further comprising means for pre-treating any one or more articles placed in the chamber before their contact with the flowing antimicrobial gas has commenced and means for post-treating any one or more articles placed in the chamber after their contact with the flowing antimicrobial gas has halted.

43. The apparatus of claim 42 wherein the means for pre-treating and the means for post-treating comprise at least some of the same members.

44. The apparatus of claim 43 further comprising an antechamber wherein the means for pre-treating and the means for post-treating each comprise the antechamber.

45. The apparatus of claim 34 further comprising means for monitoring the hydrogen peroxide concentration of the antimicrobial gas.

46. The apparatus of claim 34 further comprising means to maintain any one or more articles placed in the chamber in a predefined volume in the chamber.

47. The apparatus of claim 46 further comprising means to flow substantially all of the antimicrobial gas flowing into the chamber through the predefined volume.

48. The apparatus of claim 34 wherein the means for flowing a gas or vapor of its subparagraph (a)(3) comprises means for flowing substantially all of the first substance fed to the vaporization plenum between the inner surface of the vaporization plenum and substantially all of the fine particles to create the curtain of first substance.

49. The apparatus of claim 34 wherein the antimicrobial gas generating means is oriented so that the first direction is up and substantially vertical.

50. A method for testing sterilization processes that use a flowing antimicrobial gas comprising hydrogen peroxide vapor, or for testing materials for such processes, or for testing both such processes and such materials, the materials comprising one or more articles, the method comprising:

(a) flowing the antimicrobial gas to provide contact of any one or more articles with the antimicrobial gas when the articles are in the chamber of the apparatus of claim 30 or 38;

(b) flowing the antimicrobial gas in the chamber to contact any such one or more articles under substantially uniform conditions for the desired time, the flow of the antimicrobial gas in the chamber during the desired time being substantially continuous and the concentration of the hydrogen peroxide in the antimicrobial gas during the desired time being substantially constant as a function of time; and (c) halting the flow of antimicrobial gas after the desired time has elapsed.

51. The method of claim 50 wherein the hydrogen peroxide concentration in the antimicrobial gas during the desired time does not vary from the mean time-averaged hydrogen peroxide concentration during that time by more than plus or minus 10%.

52. The method of claim 50 wherein the hydrogen peroxide concentration in the antimicrobial gas during the desired time does not vary from the mean time-averaged hydrogen peroxide concentration during that time by more than plus or minus 8%.

53. The method of claim 30 wherein the hydrogen peroxide concentration in the antimicrobial gas during the desired time does not vary from the mean time-averaged hydrogen peroxide concentration during that time by more than plus or minus 6%.

* * * * *

UNITED STATES PATENT AND TRADEMARK OFFICE
CERTIFICATE OF CORRECTION

PATENT NO. : 7,090,808 B2  Page 1 of 1
APPLICATION NO. : 09/901389
DATED : August 15, 2006
INVENTOR(S) : Ross A. Caputo et al.

It is certified that error appears in the above-identified patent and that said Letters Patent is hereby corrected as shown below:

Column 3, line 66, change "sh" to --shall--

Claim 18, column 38, line 40, change "aas" to --gas--

Claim 18, column 38, line 66, change "aas" to --gas--

Claim 24, column 39, line 37, change "concentratiQn" to --concentration--

Claim 34, column 40, line 45, change "surface:" to --surface;--

Claim 34, column 40, line 64, change "hvdroaen" to --hydrogen--

Claim 34, column 40, line 65, change "hvdroaen" to --hydrogen--

Claim 50, column 42, line 29, change "30 or 38" to --34 or 42--

Signed and Sealed this

Twelfth Day of December, 2006

JON W. DUDAS
*Director of the United States Patent and Trademark Office*